(12) United States Patent
Tanifuji et al.

(10) Patent No.: US 8,022,207 B2
(45) Date of Patent: Sep. 20, 2011

(54) COMPOUND HAVING AFFINITY TO AMYLOID

(75) Inventors: Shigeyuki Tanifuji, Sodegaura (JP); Daisaku Nakamura, Sodegaura (JP); Shinya Takasaki, Sodegaura (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 214 days.

(21) Appl. No.: 12/226,561

(22) PCT Filed: Apr. 26, 2007

(86) PCT No.: PCT/JP2007/059048
§ 371 (c)(1), (2), (4) Date: Oct. 22, 2008

(87) PCT Pub. No.: WO2007/125988
PCT Pub. Date: Nov. 8, 2007

(65) Prior Publication Data
US 2010/0249407 A1 Sep. 30, 2010

(30) Foreign Application Priority Data
Apr. 28, 2006 (JP) ................................. 2006-124811

(51) Int. Cl.
*C07D 487/00* (2006.01)
*C07D 471/00* (2006.01)
*C07D 471/02* (2006.01)
*C07D 491/02* (2006.01)
*C07D 498/02* (2006.01)
*C07D 513/02* (2006.01)
*C07D 515/02* (2006.01)
*C07D 257/08* (2006.01)
*C07D 257/12* (2006.01)
*C07F 15/00* (2006.01)

(52) U.S. Cl. ........ 544/179; 544/184; 544/236; 544/281; 544/350; 546/121

(58) Field of Classification Search ........................ None
See application file for complete search history.

(56) References Cited

U.S. PATENT DOCUMENTS

| 2002/0022002 A1 | 2/2002 | Bario et al. |
| 2002/0133019 A1 | 9/2002 | Klunk et al. |
| 2003/0149250 A1 | 8/2003 | Kung et al. |
| 2004/0131545 A1 | 7/2004 | Kung et al. |

FOREIGN PATENT DOCUMENTS

| EP | 2 019 103 A1 | 1/2009 |
| EP | 2 042 501 A1 | 1/2009 |
| JP | 2002-523383 | 7/2002 |
| JP | 2004-506723 | 3/2004 |
| JP | 2005-504055 | 2/2005 |
| JP | 2005-512945 | 5/2005 |
| WO | WO 02/14313 A2 | 2/2002 |
| WO | WO 2008/059714 A1 | 5/2008 |
| WO | WO 2008/065785 A1 | 6/2008 |

OTHER PUBLICATIONS

Zhuang, Zhi-Ping et al., Structure-Activity Relationship of Imidazo [1,2-a]pyridines as Ligands for Detecting β-Amyloid Plaques in the Brain, J. Med. Chem., 2003, pp. 237-243, vol. 46, American Chemical Society.
European Search Report dated Aug. 28, 2009.
Office Action, dated Feb. 24, 2011, in corresponding Chinese Application 200780023153.6 (English/Chinese).

*Primary Examiner* — Jeffrey Murray
(74) *Attorney, Agent, or Firm* — Fitch, Even, Tabin & Flannery

(57) ABSTRACT

The invention relates to a compound which has affinity with amyloid, shows sufficiently rapid clearance from normal tissues and is suppressed in toxicity such as mutagenicity, and also relates to a low-toxic diagnostic agent for Alzheimer's disease containing the compound. The compound is represented by the following formula (1) or a salt thereof:

wherein $A^1$, $A^2$, $A^3$ and $A^4$ independently represent a carbon or a nitrogen, and
$R^3$ is a group represented by the following formula:

wherein $R^1$ is a radioactive halogen substituent; m is an integer of 0 to 4; and n is an integer of 0 or 1, provided that at least one of $A^1$, $A^2$, $A^3$ and $A^4$ represents a carbon, and $R^3$ binds to a carbon represented by $A^1$, $A^2$, $A^3$ or $A^4$.

8 Claims, 5 Drawing Sheets

COMPOUND HAVING AFFINITY TO AMYLOID

CROSS-REFERENCE TO RELATED APPLICATIONS

This is a U.S. National Phase of International Application PCT/JP2007/059048, filed Apr. 26, 2007, and claims the benefit of foreign priority under 35 U.S.C. §119 based on JP 2006-124811, filed Apr. 28, 2006, the entire disclosures of which applications are hereby incorporated herein by reference.

TECHNICAL FIELD

The present invention relates to a compound for use in diagnosis of cerebral degenerative disease. More specifically, the invention relates to a compound useful for amyloid detection at lesion sites in diagnosis of Alzheimer's disease and other diseases with amyloid accumulation.

BACKGROUND ART

Diseases with the onset of deposition of a fibrous protein called amyloid in various organs or tissues in bodies are generally referred to as amyloidosis. A feature common to amyloidosis is that the fibrous protein called amyloid which is enriched with the β-sheet structure is deposited at various organs systemically or at sites topically so that functional abnormalities are triggered in the organs or tissues.

Alzheimer's disease (hereinafter referred to as AD), which is a typical amyloidosis disease, is known as a disease causing dementia. This disease is lethal with progressive deposition of amyloid in brain, and thus is said to be a disease that causes concern in society compared with other amyloidosis diseases. In recent years, the number of AD patients is rapidly increasing in developed countries with aging societies, thereby causing a social problem.

From the pathohistological viewpoint, AD is characterized by three pathological findings in brain, namely development of senile plaques, formation of neurofibrillary tangles, and extensive neuronal loss. The senile plaque has a structure composed mainly of amyloid, and is said to appear at the earliest stage of AD onset and thus is pathologically found in brain about 10 or more years before appearance of clinical symptoms.

AD is diagnosed by carrying out various evaluations of cognitive functions (for example, Hasegawa scale, ADAS-JCog and MMSE) in auxiliary combination with imaging diagnosis such as CT and MRI. However, the method based on such evaluations of cognitive functions is low in diagnostic sensitivity at the early stage of the onset, and is furthermore problematic in that diagnostic results are susceptible to inborn cognitive functions of individuals. At present, it is practically impossible to establish a definite diagnosis of AD while an AD patient is still alive, because the definite diagnosis requires a biopsy of a lesion (Non-Patent Document 1).

Meanwhile, a report tells that amyloid constituting senile plaques is an aggregate of amyloid β protein (hereinafter referred to as Aβ). Also, numerous reports tell that the Aβ aggregate forms a β-sheet structure that causes nerve cell toxicity. Based on these findings, the so-called "Amyloid Cascade Hypothesis" is proposed, which suggests that cerebral deposition of Aβ triggers the downstream phenomena, namely, formation of neurofibrillary tangles and neuronal loss (Non-Patent Document 2).

Based on these facts, attempts have recently been made to detect AD in vivo using a compound having high affinity with amyloid as a marker.

Many of such probes for imaging diagnoses of cerebral amyloid are hydrophobic low-molecular compounds that are high in affinity with amyloid and high in cerebral transferability and are labeled with various radioactive species such as $^{11}C$, $^{18}F$ and $^{123}I$. For example, reports tell $^{11}C$ or radioactive halogen labeled forms of compounds including various thioflavin derivatives such as 6-iodo-2-[4'-(N,N-dimethylamino)phenyl]benzothiazole (hereinafter referred to as TZDM) and 6-hydroxy-2-[4'-(N-methylamino)phenyl]benzothiazole (hereinafter referred to as 6-OH-BTA-1) (Patent Document 1, Non-Patent Document 3); stilbene compounds such as (E)-4-methylamino-4'-hydroxystilbene (hereinafter referred to as SB-13) and (E)-4-dimethylamino-4'-iodostilbene (hereinafter referred to as m-I-SB) (Patent Document 2, Non-Patent Document 4, Non-Patent Document 5); benzoxazole derivatives such as 6-iodo-2-[4'-(N,N-dimethylamino) phenyl]benzoxazole (hereinafter referred to as IBOX) and 6-[2-(fluoro)ethoxy]-2-[2-(2-dimethylaminothiazol-5-yl) ethenyl]benzoxazole (Non-Patent Document 6, Non-Patent Document 7), DDNP derivatives such as 2-(1-{6-[(2-fluoroethyl)(methyl)amino]-2-naphthyl}ethylidene)malononitrile (hereinafter referred to as FDDNP) (Patent Document 4, Non-Patent Document 8); and imidazopyridine derivatives such as 6-iodo-2-[4'-(N,N-dimethylamino)phenyl]imidazo[1,2-a]pyridine (hereinafter referred to as IMPY) (Patent Document 3, Non-Patent Document 9). Further, some of these probes for imaging diagnosis have been studied on human imaging and have been reported to show a significant accumulation in AD patient's brain compared with normal persons (Non-Patent Document 10, Non-Patent Document 11).

[Patent Document 1] JP-T-2004-506723
[Patent Document 2] JP-T-2005-504055
[Patent Document 3] JP-T-2005-512945
[Patent Document 4] JP-T-2002-523383
[Non-Patent Document 1] J. A. Hardy & G. A. Higgins, "Alzheimer's Disease: The Amyloid Cascade Hypothesis.", Science, 1992, 256, p. 184-185
[Non-Patent Document 2] G. McKhann et al., "Clinical diagnosis of Alzheimer's disease: Report of the NINCDS-ADRDA Work Group under the auspices of Department of Health and Human Services Task Force on Alzheimer's Disease.", Neurology, 1984, 34, p. 939-944
[Non-Patent Document 3] Z.-P. Zhuang et al., "Radioiodinated Styrylbenzenes and Thioflavins as Probes for Amyloid Aggregates.", J. Med. Chem., 2001, 44, p. 1905-1914
[Non-Patent Document 4] Masahiro Ono et al., "11C-labeled stilbene derivatives as Aβ-aggregate-specific PET imaging agents for Alzheimer's disease.", Nuclear Medicine and Biology, 2003, 30, p. 565-571
[Non-Patent Document 5] H. F. Kung et al., "Novel Stilbenes as Probes for amyloid plaques.", J. American Chemical Society, 2001, 123, p. 12740-12741
[Non-Patent Document 6] Zhi-Ping Zhuang et al., "IBOX(2-(4'-dimethylaminophenyl)-6-iodobensoxazole): a ligand for imaging amyloid plaques in the brain.", Nuclear Medicine and Biology, 2001, 28, p. 887-894
[Non-Patent Document 7] Furumoto Y et al., "[$^{11}C$]BF-227: A New $^{11}C$-Labeled 2-Ethenylbenzoxazole Derivative for Amyloid-β Plaques Imaging.", European Journal of Nuclear Medicine and Molecular Imaging, 2005, 32, Sup. 1, P 759
[Non-Patent Document 8] Eric D. Agdeppa et al., "2-Dialkylamino-6-Acylmalononitrile Substituted Naphthalenes (DDNP Analogs): Novel Diagnostic and Therapeutic Tools in Alzheimer's Disease.", Molecular Imaging and Biology, 2003, 5, p. 404-417

[Non-Patent Document 9]-Zhi-Ping Zhuang et al., "Structure-Activity Relationship of Imidazo[1,2-a]pyridines as Ligands for Detecting β-Amyloid Plaques in the Brain.", J. Med. Chem, 2003, 46, p. 237-243

[Non-Patent Document 10] W. E. Klunk et al., "Imaging brain amyloid in Alzheimer's disease with Pittsburgh Compound-B.", Ann. Neurol., 2004, 55, p. 306-319

[Non-Patent Document 11] Nicolaas P. L. G. Verhoeff et al., "In-Vivo Imaging of Alzheimer Disease β-Amyloid With [11C]SB-13 PET.", American Journal of Geriatric Psychiatry, 2004, 12, p. 584-595

DISCLOSURE OF THE INVENTION

Problems to be Solved by the Invention

As described above, various compounds are disclosed as probes for imaging diagnosis for amyloid, and researched for clinical application.

Experiments in normal mice show that [$^{125}$I]-labeled TZDM, IBOX and m-I-SB are all transferred into brain 2 minutes after administration. However, these compounds are insufficient in clearance from normal tissues, and tend to accumulate gradually in brain as time passes after administration (JP-T-2005-512945; Zhi-Ping Zhuang et al., Nuclear Medicine and Biology, 2001, 28, p. 887-894; H. F. Kung et al., J. Am. Chem. Soc., 2001, 123, p. 12740-12741). When the clearance from normal tissues is insufficient, a problem arises in that sufficient contrast cannot be obtained at amyloid accumulation sites. [$^{11}$C]-labeled SB-13 shows a clearance from normal tissues in experiments in rats, however, it cannot be said that the clearance is sufficiently fast (Masahiro Ono et al., Nuclear Medicine and Biology, 2003, 30, p. 565-571).

Meanwhile, it is revealed that compounds having an imidazopyridine skeleton such as IMPY have a property of transferring to brain and accumulating at amyloid after administration, and also have an excellent property of rapid clearance from normal tissues unlike the above-described compounds, as a result of experiments using [$^{125}$I]-labeled compounds. However, IMPY is a compound positive in reverse mutation test. In order to use this compound as a probe for imaging diagnosis, sufficient care must be taken about dosage and administration manner. (International Publication WO03/106439 pamphlet)

FDDNP is also reported to be positive in reverse mutation test. (International Publication WO03/106439 pamphlet)

A preferable probe targeting amyloid for imaging diagnosis would be a compound that is excellent in affinity with amyloid and sufficiently rapid in clearance from normal tissues like IMPY but is suppressed in toxicity such as mutagenicity. However, no compound with such properties has been disclosed.

The present invention has been made under such circumstances, and aims at providing a compound that has affinity with amyloid, exhibits sufficiently rapid clearance from normal tissues and is suppressed in toxicity such as mutagenicity, and also providing a diagnostic agent for Alzheimer's disease.

Means for Solving the Problems

The inventors have found that a group of compounds satisfying the above-described requirements can be obtained from a compound with an imidazopyridine-phenyl skeleton having a carbon atom to which hydroxyl group is attached, and thus have completed the present invention.

Specifically, the present invention relates to a compound represented by the following formula (1):

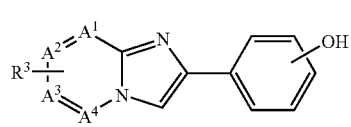

(1)

or a salt thereof, and a low-toxic diagnostic agent for Alzheimer's disease comprising a compound represented by the above formula (1) or a salt thereof.

In the formula (1), $R^3$ is a group represented by

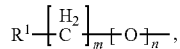

$R^1$ is a radioactive halogen substituent, m is an integer of 0 to 4 and n is 0 or 1. As the radioactive halogen, various elements can be used, preferably a halogen selected from the group consisting of $^{18}$F, $^{76}$Br, $^{123}$I, $^{124}$I, $^{125}$I and $^{131}$I, and more preferably a halogen selected from the group consisting of $^{18}$F, $^{123}$I and $^{125}$I. In the formula (1), when n=0, m=0 to 4 is preferable, and when n=1, m=1 to 4 is preferable.

$A^1$, $A^2$, $A^3$ and $A^4$ independently represent a carbon or nitrogen, and it is necessary that at least one of these represents a carbon. Preferably, 3 or more of $A^1$, $A^2$, $A^3$ and $A^4$ represent carbons, and more preferably, all of them represent carbons. In the formula (1), $R^3$ binds to a carbon represented by $A^1$, $A^2$, $A^3$ or $A^4$. When $A^1$, $A^2$, $A^3$ and $A^4$ respectively represent a carbon which is not bound to $R^3$, a hydrogen atom binding thereto is to be unsubstituted. A hydroxyl group indicated in the formula (1) may bind to any of the carbons constituting the phenyl skeleton thereof, but it is preferable that the hydroxyl group binds to a carbon at 4'-position of the phenyl skeleton. A binding site for $R^3$ may be any of $A^1$, $A^2$, $A^3$ and $A^4$ as long as it is a carbon, but is preferably a carbon represented by $A^3$, that is, a carbon at 6-position.

According to another aspect of the present invention, a compound represented by the following formula (2):

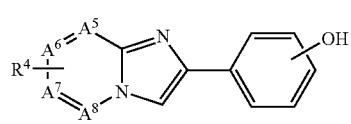

(2)

or a salt thereof is provided.

In the formula (2), $R^4$ is a group represented by

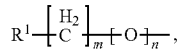

m is an integer of 0 to 4, n is 0 or 1, and when m=n=0, $R^2$ is a non-radioactive halogen substituent, nitro substituent, trialkylstannyl substituent having from 3 to 12 carbon atoms or triphenylstannyl substituent, and when m≠0 and/or n≠0, it is a non-radioactive halogen substituent, methanesulfonyloxy substituent, trifluoromethanesulfonyloxy substituent or aromatic sulfonyloxy substituent. As the non-radioactive halogen substituent, a halogen capable of being a target of nucleophilic substitution reactions using a radioactive fluorine or a halogen capable of being a target of isotope exchange reactions with a radioactive iodine can be used, and preferably iodine, bromine or chlorine can be used. As the trialkylstannyl substituent, various substituents can be used, and preferably trimethylstannyl substituent and tributylstannyl substituent can be used. In the formula (2), when n=0, m=0 to 4 is preferable, and when n=1, m=1 to 4 is preferable.

$A^5$, $A^6$, $A^7$ and $A^8$ independently represent a carbon or nitrogen, and it is necessary that at least one of these represents a carbon. Preferably, 3 or more of $A^5$, $A^6$, $A^7$ and $A^8$ represent carbons, and more preferably, all of them represent carbons. In the formula (2), $R^4$ binds to a carbon represented by $A^5$, $A^6$, $A^7$ or $A^8$. When $A^5$, $A^6$, $A^7$ and $A^8$ respectively represent a carbon which is not bound to $R^4$, a hydrogen atom binding thereto is to be unsubstituted. A hydroxyl group indicated in the formula (2) may bind to any of the carbons constituting the phenyl skeleton thereof, but it is preferable that the hydroxyl group binds to a carbon at 4'-position of the phenyl skeleton. A binding site for $R^4$ may be any of $A^5$, $A^6$, $A^7$ and $A^8$ as long as it is a carbon, but is preferably a carbon represented by $A^7$, that is, a carbon at 6-position.

Effects of the Invention

In accordance with the present invention, a compound that has affinity with amyloid and is sufficiently fast in clearance from normal tissues and suppressed in toxicity such as mutagenicity can be obtained as well as a diagnostic agent for Alzheimer's disease with low toxicity.

BEST MODE FOR CARRYING OUT THE INVENTION

Hereinafter, a method for synthesis of a precursor compound for a radioactive halogen-labeled compound according to an aspect of the present invention will be described, taking the case of 6-tributylstannyl-2-[4'-hydroxyphenyl]imidazo[1,2-a]pyridine.

First, 4'-hydroxyacetophenone is allowed to react with cupric bromide to prepare 2-bromo-4'-hydroxyacetophenone (FIG. 1, Step 1). In this instance, the reaction can be conducted in accordance with ordinary methods, for example, the method described in a literature, King, L. Carroll and Ostrum, G. Kenneth, Journal of Organic Chemistry, 1964, 29(12), p. 3459-3461.

Then, 2-bromo-4'-hydroxyacetophenone as prepared above is allowed to react with 2-amino-5-bromopyridine to prepare 6-bromo-2-(4'-hydroxyphenyl)imidazo[1,2-a]pyridine (FIG. 1, Step 2). This step can be done according to the following procedure.

First, 2-bromo-4'-hydroxyacetophenone and 2-amino-5-bromopyridine are dissolved in an inactive solvent such as acetonitrile, and are allowed to react with each other at a reflux temperature for 2 to 6 hours to produce 6-bromo-2-(4'-hydroxyphenyl)imidazo[1,2-a]pyridine hydrobromide salt as white precipitates. The solvent used in this instance may be acetonitrile or another solvent that is usually employed in a similar reaction, for example, methanol and acetone. The reaction temperature may be a temperature allowing refluxing, for example, 90° C. when the solvent is acetonitrile. The amount of the solvent to be used may be an amount sufficient to effect the reaction, however, it should be noted that if the solvent is too much, it will become difficult to obtain precipitates of reaction products. For example, when 2-bromo-4'-hydroxyacetophenone in an amount corresponding to 10 mmol is used for the reaction, the amount of a solvent to be used can be about 40 to 50 mL.

Next, the reaction solution is filtered to recover the precipitates. The white precipitates are suspended in a mixed solution of methanol/water (1:1). Then, an aqueous saturated solution of sodium hydrogencarbonate is added thereto in a very excessive amount relative to the suspended precipitates to release 6-bromo-2-(4'-hydroxyphenyl)imidazo[1,2-a]pyridine as precipitates. The newly generated precipitates are filtered to recover 6-bromo-2-(4'-hydroxyphenyl)imidazo[1,2-a]pyridine as the target compound in this step (FIG. 1, Step 2). The amount of the mixed solution of water/methanol is not specifically limited as long as it is sufficient to effect the reaction. However, it should be noted that if the amount of the mixed solution is too much, precipitation of products will be hindered. For example, when 2-bromo-4'-hydroxyacetophenone in an amount corresponding to 10 mmol is used, the mixed solution of water/methanol may be used in an amount of about 40 to 100 mL. The amount of sodium hydrogencarbonate is not specifically limited as long as it is very excessive relative to the above-described precipitates as reaction substrates. For example, when the reaction is effected under the above-described conditions, the amount of an aqueous saturated solution of sodium hydrogencarbonate to be added to the reaction solution can be about 25 mL.

Then, the 6-bromo-2-(4'-hydroxyphenyl)imidazo[1,2-a]pyridine prepared above is sufficiently dried, dissolved in dioxane, and after triethylamine is added, bis(tributyltin) and a catalytic amount of tetrakis-triphenylphosphine palladium are added. This reaction mixture is heated at about 90° C. and reacted for about 24 hours, and then a solvent is distilled off and a chromatographic purification is performed to obtain 6-tributylstannyl-2-[4'-hydroxyphenyl]imidazo[1,2-a]pyridine as the target compound (FIG. 1, Step 3). The amount of bis(tributyltin) to be used is an amount satisfying a condition where it is excessive relative to the reaction substrate, specifically, it is preferably about 1.5 times in molar ratio relative to the 6-bromo-2-(4'-hydroxyphenyl)imidazo[1,2-a]pyridine as the reaction substrate.

When a compound with a substituent at the 6-position being a trialkylstannyl substituent other than tributylstannyl substituent is obtained, various bis(trialkyltin)s that fit purposes can be used instead of bis(tributyltin) in Step 3. For example, when a compound having a trimethylstannyl substituent as a substituent at the 6-position is synthesized, a reaction similar to the above can be performed in Step 3 using bis(trimethyltin).

In order to obtain a compound with a substituent at the 6-position being a non-radioactive halogen substituent, the compound obtained in Step 2 per se may be used as a compound having bromine as the halogen substituent, and for compounds having fluorine, chlorine and iodine as the halogen substituent at the 6-position, the same reaction as in Step 2 may be performed except using 2-amino-5-fluoropyridine, 2-amino-5-chloropyridine and 2-amino-5-iodopyridine respectively instead of 2-amino-5-bromopyridine in Step 2.

In order to obtain a compound with a substituent at the 6-position being attached thereto via oxygen atom, 2-amino-5-hydroxypyridine instead of 2-amino-5-bromopyridine may be reacted to synthesize 2-(4'-hydroxyphenyl)-6-hydroxyimidazo[1,2-a]pyridine, and a bromide compound having a substituent desired to be introduced may be reacted therewith in the presence of a base. For example, in order to obtain a compound having a 3-fluoropropoxy substituent at the 6-position, 2-(4'-hydroxyphenyl)-6-hydroxyimidazo[1,2-a]pyridine can be reacted with 1-bromo-3-fluoropropane in the presence of potassium carbonate.

Further, in order to obtain a compound with a substituent at the 6-position being attached thereto via an alkyl chain, the following operations can be performed. For example, for a compound with a substituent at the 6-position being a 3'-bromopropyl group, 2-(4'-hydroxyphenyl)-6-bromoimidazo[1,2-a]pyridine obtained in Step 2 may be reacted with allyltributyltin, and converted to 6-allyl-2-(4'-hydroxyphenyl)imidazo[1,2-a]pyridine. Then, it is subjected to hydroboronation and oxidation reactions so as to be converted to 2-(4'-hydroxyphenyl)-6-(3'-hydroxypropyl)imidazo[1,2-a]pyridine. Furthermore, bromination of the hydroxyl group by tetrabromomethane may be performed in the presence of triphenylphosphine.

Compounds represented by the above formula (1) in which $A^1$ among $A^1$, $A^2$, $A^3$ and $A^4$ is a nitrogen, and compounds represented by the above formula (2) in which $A^5$ among $A^5$, $A^6$, $A^7$ and $A^8$ is a nitrogen can be produced in accordance with the above method except using 2-amino-5-bromopyrimidine instead of 2-amino-5-bromopyridine in Step 2 of FIG. 1.

Compounds represented by the above formula (1) in which $A^2$ and $A^4$ among $A^1$, $A^2$, $A^3$ and $A^4$ are nitrogens, and compounds represented by the above formula (2) in which $A^6$ and $A^8$ among $A^5$, $A^6$, $A^7$ and $A^8$ are nitrogens can be produced in accordance with the above method except using 6-amino-3-bromo-1,2,4-triazine instead of 2-amino-5-bromopyridine in Step 2 of FIG. 1.

Hereinafter, a method for production of a radioactive halogen-labeled compound according to another aspect of the present invention will be described by taking the case of 2-[4'-hydroxyphenyl]-6-[$^{123}$I]iodoimidazo[1,2-a]pyridine.

For the production of 2-[4'-hydroxyphenyl]-6-[$^{123}$I]iodoimidazo[1,2-a]pyridine, a [$^{123}$I]sodium iodide solution to be served for labeling is first obtained. A [$^{123}$I] radioactive iodine can be obtained by, for example, a known method in which a xenon gas is used as a target and exposed to proton bombardment. This [$^{123}$I]radioactive iodine is made into [$^{123}$I] sodium iodide solution by using known methods, and used for the labeling.

Then, the labeling precursor 6-tributylstannyl-2-[4'-hydroxyphenyl]imidazo[1,2-a]pyridine is dissolved in an inert organic solvent, and the [$^{123}$I]sodium iodine solution, an acid and an oxidizing agent are added thereto and allowed to react to obtain 2-[4'-hydroxyphenyl]-6-[$^{123}$I]iodoimidazo[1,2-a] pyridine as a target compound. As the inert organic solvent dissolving the precursor compound, various solvents having no reactivity with the labeling precursor and the [$^{123}$I]sodium iodide can be used, and preferably methanol can be used.

As the acid, may be used various ones, and preferably hydrochloric acid.

The oxidizing agent is not particularly limited as long as it can effect the oxidation of iodine in the reaction solution, and is preferably hydrogen peroxide or peracetic acid. The amount of the oxidizing agent to be added may be an amount sufficient to oxidize iodine in the reaction solution.

A compound labeled with a radioactive halogen other than iodine can be synthesized by labeling a labeling precursor that fits a purpose of synthesis with a radioactive halogen that fits the purpose. For example, in order to synthesize 6-[$^{18}$F]fluoropropoxy-2-(4'-hydroxyphenyl)imidazo[1,2-a]pyridine, the labeling precursor 2-(4'-hydroxyphenyl)-6-(3'-p-toluenesulfonyloxypropoxy)imidazo[1,2-a]pyridine can be reacted with [$^{18}$F]fluoride ion in the presence of a phase transfer catalyst and potassium carbonate.

The diagnostic agent according to the present invention can be prepared as a solution which comprises the present radioactive halogen-labeled compound blended in water, a physiological saline solution or a Ringer's solution optionally adjusted to an appropriate pH, like other commonly-known radioactive diagnostic agents. In this instance, concentration of the present compound should be adjusted to not more than the concentration at which stability of the present compound is ensured. Dosage of the present compound is not specifically limited as long as it is sufficient to obtain an image of distribution of an administered agent. For example, in case of iodine-123-labeled compounds and fluorine-18-labeled compounds, about 50 to 600 MBq per adult body of 60 kg weight can be administered intravenously or locally. Distribution of administered agents can be imaged by known methods. For example, iodine-123-labeled compounds can be imaged by a SPECT apparatus while fluorine-18-labeled compounds can be imaged by a PET apparatus.

EXAMPLE

Hereinafter, the present invention is described below in more detail by way of Examples, Comparative Examples and Reference Examples. However, these Examples never limit the scope of the present invention.

In the following Examples, the names of the individual compounds used in the experiment are defined as shown in Table 1.

TABLE 1

Names of compounds used for evaluation in Examples

| Compound name | Common name |
|---|---|
| Compound 1 | 6-bromo-2-(4'-hydroxyphenyl)imidazo[1,2-a]pyridine |
| Compound 2 | 2-(4'-hydroxyphenyl)-6-iodoimidazo[1,2-a]pyridine |
| Compound 3 | 6-(3'-fluoropropoxy)-2-(4'-hydroxyphenyl)imidazo[1,2-a]pyridine |
| Compound 4 | 2-(4'-hydroxyphenyl)-6-iodoimidazo[1,2-a]pyrimidine |
| Compound 5 | [$^{125}$I]-2-(4'-hydroxyphenyl)-6-iodoimidazo[1,2-a]pyridine |
| Compound 6 | [$^{123}$I]-2-(4'-hydroxyphenyl)-6-iodoimidazo[1,2-a]pyridine |
| Compound 7 | 6-bromo-2-(4'-hydroxyphenyl)imidazo[1,2-a]pyrazine |
| Compound 8 | 2-(4'-hydroxyphenyl)-6-iodoimidazo[1,2-a]pyrazine |
| Compound 9 | [$^{123}$I]-2-(4'-hydroxyphenyl)-6-iodoimidazo[1,2-a]pyrimidine |
| Compound 10 | [$^{123}$I]-2-(4'-hydroxyphenyl)-6-iodoimidazo[1,2-a]pyrazine |
| Compound 11 | [$^{123}$I]-2-(4'-hydroxyphenyl)-8-iodoimidazo[1,2-a]pyridine |

Example I-1

Synthesis of 6-tributylstannyl-2-(4'-hydroxyphenyl) imidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction solution was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent:chloroform/methanol=20/1), and recrystallized from ethyl acetate/petroleum ether, to obtain 7.25 g (corresponding to 33.7 mmol) of 2-bromo-4'-hydroxyacetophenone (FIG. 1, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 1, Step 2).

138 mg (corresponding to 0.476 mmol) of 6-bromo-2-(4'-hydroxyphenyl)imidazo[1,2-a]pyridine was dissolved in 20 mL of dioxane, and 2 mL of triethylamine was added thereto. Then, 360 μL (corresponding to 0.713 mmol) of bis(tributyltin) and 20 mg (at a catalytic amount) of tetrakis-triphenylphosphine palladium were added. After the reaction mixture was stirred at 90° C. for 22 hours, the solvent was distilled off under reduced pressure. The residue was purified by preparative TLC (elution solvent:hexane/ethyl acetate=1/4). Further, the resulting crude product was purified by recycle preparative HPLC (HPLC apparatus: LC-908 (under trade name; manufactured by Japan Analytical Industry Co., Ltd.); column: two of JAIGEL 2H (under trade name; manufactured by Japan Analytical Industry Co., Ltd.) connected together; mobile phase: chloroform), to obtain 47 mg (corresponding to 94.9 μmol) of 6-tributylstannyl-2-(4'-hydroxyphenyl)imidazo[1,2-a]pyridine (FIG. 1, Step 3).

The NMR measurement results of the resulting 6-tributylstannyl-2-(4'-hydroxyphenyl)imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.01-7.94 (m, 1H), 7.71-7.67 (m, 2H), 7.70-7.67 (m, 1H), 7.64-7.60 (m, 1H), 7.20-7.11 (m, 1H), 6.89-6.85 (m, 2H), 1.62-1.46 (m, 6H), 1.34 (sext, J=7.3 Hz, 6H), 1.18-1.03 (m, 6H), 0.90 (t, J=7.3 Hz, 9H).

$^{13}$C-NMR (solvent: chloroform-dl, resonance frequency: 125 MHz): δ 157.85, 145.11, 144.72, 131.90, 129.93, 127.62, 124.02, 122.59, 116.14, 116.09, 106.19, 28.96, 27.27, 13.62, 9.81.

Example I-2

Synthesis of [$^{125}$I]-2-(4'-hydroxyphenyl)-6-iodoimidazo[1,2-a]pyridine

To 53 μL of a solution of 6-tributylstannyl-2-(4'-hydroxyphenyl)imidazo[1,2-a]pyridine in methanol (concentration: 1 mg/mL), 75 μL of 1 mol/L hydrochloric acid, [$^{125}$I]sodium iodide of 136 MBq (40 μL in volume) and 10 μL of 10% (w/v) hydrogen peroxide were added. After the mixed solution was left to stand at 50° C. for 10 minutes, the solution was subjected to HPLC under the following conditions, to obtain [$^{125}$I]-2-(4'-hydroxyphenyl)-6-iodoimidazo[1,2-a]pyridine fraction.

HPLC Conditions:

Column: Phenomenex Luna C18 (trade name; manufactured by Phenomenex Co.; size: 4.6×150 mm)

Mobile phase: 0.1% trifluoroacetic acid/acetonitrile=20/80 to 0/100 (17 minutes, linear gradient)

Flow rate: 1.0 mL/min.

Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark, Waters Investments Limited) Light C18 Cartridges manufactured by Waters: the packed amount of the packing agent: 130 mg) so that the column adsorbs and collects [$^{125}$I]-2-(4'-hydroxyphenyl)-6-iodoimidazo[1,2-a]pyridine. The column was rinsed with 1 mL of water, and then 1 mL of ethanol was passed therethrough to elute [$^{125}$I]-2-(4'-hydroxyphenyl)-6-iodoimidazo[1,2-a]pyridine. The amount of radioactivity of the obtained compound was 37.5 MBq at the end of synthesis. Further, the TLC analysis was conducted under the following conditions, and as a result, the radiochemical purity of the compound was 96.5%.

TLC Analysis Conditions:

TLC plate: RP-18F254 (trade name; manufactured by Merck & Co., Inc.)

Mobile phase: Methanol/water=20/1

Detector: Bio-imaging Analyzer, BAS-2500 (type: BAS-2500 manufactured by FUJIFILM Corporation)

Example I-3

Synthesis of [$^{123}$I]-2-(4'-hydroxyphenyl)-6-iodoimidazo[1,2-a]pyridine

To 70 μL of a solution of 6-tributylstannyl-2-(4'-hydroxyphenyl)imidazo[1,2-a]pyridine in methanol (concentration: 1 mg/mL), 75-100 μL of 1 mol/L hydrochloric acid, [$^{123}$I] sodium iodide of 236-454 MBq (15-120 μL in volume) and 7.5-10 μL of 1 mmol/L sodium iodide solution and 10-15 μL of 10% (w/v) hydrogen peroxide were added. After the mixed solution was heated at 50° C. for 10 minutes, the solution was subjected to HPLC under the same conditions as in Example I-2, to obtain [$^{123}$I]-2-(4'-hydroxyphenyl)-6-iodoimidazo[1,2-a]pyridine as a fraction.

10 ml of water was added to the fraction. The resulting solution was passed through a reversed phase column (trade name: Sep-Pak (registered trademark, Waters Investments Limited) Light C18 Cartridges manufactured by Waters: the packed amount of the packing agent: 130 mg) so that the column adsorbs and collects [$^{123}$I]-2-(4'-hydroxyphenyl)-6-iodoimidazo[1,2-a]pyridine. The column was rinsed with 1 mL of water, and then 1 mL of diethyl ether was passed therethrough, to elute [$^{123}$I]-2-(4'-hydroxyphenyl)-6-iodoimidazo[1,2-a]pyridine. The amount of radioactivity of the obtained compound was 21-180 MBq at the end of synthesis. Further, the TLC analysis was conducted under the same conditions as in Example I-2, and as a result, the radiochemical purity of the compound was 99.5%.

Example I-4

Synthesis of 6-bromo-2-(4'-hydroxyphenyl)imidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction solution was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether to obtain 7.25 g (corresponding to 33.7 mmol) of 2-bromo-4'-hydroxyacetophenone (FIG. 2, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 2, Step 2).

The NMR measurement results of the resulting 6-bromo-2-(4'-hydroxyphenyl)imidazo[1,2-a]pyridine (internal standard: dimethylsulfoxide) are shown below.

NMR apparatus employed: JNM-ECP-500 (manufactured by Japan Electron Optics Laboratory Co., Ltd. (JEOL))

$^1$H-NMR (solvent: dimethylsulfoxide-d6, resonance frequency: 500 MHz): δ 9.54 (br. s, 1H), 8.83-8.81 (m, 1H), 8.17 (s, 1H), 7.79-7.74 (m, 2H), 7.51 (d, J=9.6 Hz, 1H), 7.30 (dd, J=9.6, 1.8 Hz, 1H), 6.86-6.81 (m, 2H).

$^{13}$C-NMR (solvent: dimethylsulfoxide-d6, resonance frequency: 125 MHz): δ 158.15, 146.40, 143.79, 127.82, 127.67, 127.14, 125.01, 117.87, 116.15, 108.60, 106.05.

Example I-5

Synthesis of 2-(4'-hydroxyphenyl)-6-iodoimidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction solution was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 3, Step 1).

441 mg (corresponding to 2.0 mmol) of 2-bromo-4'-hydroxyacetophenone and 449 mg (corresponding to 2.0 mmol) of 2-amino-5-iodopyridine were dissolved in 15 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 526 mg (corresponding to 1.56 mmol) of 2-(4'-hydroxyphenyl)-6-iodoimidazo[1,2-a]pyridine (FIG. 3, Step 2).

The NMR measurement results of the resulting 2-(4'-hydroxyphenyl)-6-iodoimidazo[1,2-a]pyridine (internal standard: dimethylsulfoxide) are shown below.

NMR apparatus employed: JNM-ECP-500 (manufactured by Japan Electron Optics Laboratory Co., Ltd. (JEOL))

$^1$H-NMR (solvent: dimethylsulfoxide-d6, resonance frequency: 500 MHz): δ 8.86-8.84 (m, 1H), 8.14 (s, 1H), 7.78-7.74 (m, 2H), 7.40-7.35 (m, 2H), 6.86-6.82 (m, 2H).

$^{13}$C-NMR (solvent: dimethylsulfoxide-d6, resonance frequency: 125 MHz): δ 158.08, 145.87, 143.87, 132.48, 131.72, 127.67, 124.99, 118.14, 116.14, 108.02, 75.85.

Example I-6

Synthesis of 2-(4'-hydroxyphenyl)-6-iodoimidazo[1,2-a]pyrimidine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 4, Step 1).

646 mg (corresponding to 3.0 mmol) of 2-bromo-4'-hydroxyacetophenone and 668 mg (corresponding to 3.0 mmol) of 2-amino-5-iodopyrimidine were dissolved in 20 mL of acetonitrile. The resulting solution was refluxed in an oil bath at 110° C. for 8 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 15 mL of a saturated sodium hydrogencarbonate solution was added thereto, and the mixture was sonicated for 3 minutes using an ultrasonic washing machine. Precipitates were filtered and recovered from the resulting mixture, sufficiently washed with water, and dried under reduced pressure, to obtain 737 mg (corresponding to 2.19 mmol) of 2-(4'-hydroxyphenyl)-6-iodoimidazo[1,2-a]pyrimidine (FIG. 4, Step 2).

The NMR measurement results of the resulting 2-(4'-hydroxyphanyl)-6-iodoimidazo[1,2-a]pyrimidine (internal standard: dimethylformamide) are shown below.

NMR apparatus employed: JNM-ECP-500 (manufactured by Japan Electron Optics Laboratory Co., Ltd. (JEOL))

$^1$H-NMR (solvent: dimethylformamide-d7, resonance frequency: 500 MHz): δ 9.80 (br. s, 1H), 9.35 (d, J=2.3 Hz, 1H), 8.60 (d, J=2.3 Hz, 1H), 8.23 (s, 1H), 7.94-7.90 (m, 2H), 6.98-6.94 (m, 2H).

$^{13}$C-NMR (solvent: dimethylformamide-d7, resonance frequency: 125 MHz): δ 158.87, 154.00, 147.18, 146.77, 139.07, 127.68, 124.50, 115.85, 106.10, 73.46.

Example I-7

Synthesis of 6-(3'-fluoropropoxy)-2-(4'-hydroxyphenyl)imidazo[1,2-a]pyridine 31.11 g (corresponding to 178.88 mmol) of 2-bromo-3-hydroxypyridine was dissolved in 95.8 mL of dimethylsulfoxide, and 89.9 mL (corresponding to 89.9 mmol) of 1 mol/L sodium methoxide-methanol solution was added thereto. Then, the reaction solution was heated to 90° C. to distill off methanol. After the reaction solution was cooled down to 5° C. or lower, 29.2 g (corresponding to 205.62 mmol) of methyl iodide was added, and then stirred at room temperature for 17 hours. After the completion of the reaction, the reaction solution was poured into ice water and extracted twice with chloroform. The combined chloroform layer was washed with 1 mol/L sodium hydroxide solution, washed twice with a saturated sodium chloride solution, and dried over anhydrous sodium sulfate. After the solvent was distilled off under reduced pressure, 20.74 g (corresponding to 110.31 mmol) of 2-bromo-3-methoxypyridine was obtained (FIG. 5, Step 1).

83 mL of conc. sulfuric acid was cooled down to −5° C., and 83 mL of 90% nitric acid was carefully added thereto. Subsequently, 20.69 g (corresponding to 110.04 mmol) of 2-bromo-3-methoxypyridine was carefully added thereto. After the reaction mixture was stirred in an ice bath for 5 minutes, the mixture was stirred at room temperature for 10 minutes, and then was heated to 55° C. and further stirred for an hour. After the reaction solution was cooled to room temperature, the reaction solution was poured little by little into crushed ice to generate precipitates. The precipitates were filtered and washed with water, and then dried over phosphorous pentoxide under reduced pressure, to obtain 17.41 g (corresponding to 74.71 mmol) of 2-bromo-3-methoxy-6-nitropyridine (FIG. 5, Step 2).

17.36 g (corresponding to 74.50 mmol) of 2-bromo-3-methoxy-6-nitropyridine was dissolved in 520 mL of ethanol, and 11.63 g (50% wet) of 10% palladium-carbon was added thereto under argon atmosphere. To the mixture, 88.4 mL of hydrazine monohydrate was added dropwise. After the reaction mixture was refluxed for 45 minutes, the reaction solution was cooled down to room temperature. Then, after palladium-carbon was filtered off, the residue was washed with ethanol, and the washings were combined with the filtrate. The combined solution was concentrated under reduced pressure. Then, 402 mL of water and 38 mL of conc. aqueous ammonia were added to the concentrate, and the resulting mixture was extracted eight times with chloroform. The combined chloroform layer was dried over anhydrous sodium sulfate and concentrated under reduced pressure. The resulting crude product was distilled under reduced pressure to obtain 8.14 g (corresponding to 65.57 mmol) of 2-amino-5-methoxypyridine (FIG. 5, Step 3).

13.50 g (corresponding to 59.66 mmol) of 4'-benzoyloxyacetophenone was dissolved in 1100 ml of methanol, and 34.52 g (corresponding to 71.59 mmol) of tetra-n-butylammonium tribromide was added thereto. The mixture was stirred overnight at room temperature, and was distilled off under reduced pressure to remove the solvent. The residue was dissolved in ethyl acetate and washed twice with water and then washed with an aqueous saturated sodium chloride solution. After the ethyl acetate layer was dried over anhydrous sodium sulfate and concentrated under reduced pressure, the resulting crude product was purified by silica gel column chromatography (elution solvent: hexane/methylene chloride=1/1), to obtain 13.38 g (corresponding to 43.84 mmol) of 4'-benzoyloxy-2-bromoacetophenone (FIG. 5, Step 4).

13.33 g (corresponding to 43.68 mmol) of 4'-benzoyloxy-2-bromoacetophenone and 5.67 g (corresponding to 45.67 mmol) of 2-amino-5-methoxypyridine were dissolved in 481 mL of ethanol. The resulting solution was refluxed for 2 hours. After the reaction solution was cooled, 6.64 g (corresponding to 79.09 mmol) of sodium hydrogencarbonate was added thereto. The resulting reaction mixture was further refluxed for 4 hours. After the completion of the reaction, the solvent was concentrated under reduced pressure. The resulting residue was dissolved in chloroform and then washed with water. After the chloroform layer was dried over anhydrous sodium sulfate, the solvent was distilled off. The resulting crude product was purified by silica gel column chromatography (elution solvent: chloroform/ethyl acetate=20/1), to obtain 10.20 g (corresponding to 30.87 mmol) of 2-(4'-benzoyloxyphenyl)-6-methoxyimidazo[1,2-a]pyridine (FIG. 5, Step 5).

4.90 g (corresponding to 14.83 mmol) of 2-(4'-benzoyloxyphenyl)-6-methoxyimidazo[1,2-a]pyridine that was sufficiently dried to remove moisture was dissolved in 245 mL of chloroform and cooled down to −15° C. To this solution, a solution of 12.62 mL (corresponding to 133.48 mmol) of boron tribromide in 134 mL of dichloromethane was added dropwise. After the temperature of the resulting solution was raised to room temperature, the solution was stirred for 17 hours. After the completion of the reaction, the reaction solution was cooled with ice and supplemented with 668 mL of methanol, and further stirred at room temperature for 3 hours. The reaction mixture was then concentrated under reduced pressure. The resulting crude product was supplemented with 290 mL of chloroform and 29 mL of methanol to obtain slurry, and then precipitates were filtered and recovered. The precipitates recovered were washed with chloroform and then dried under reduced pressure, to obtain 3.00 g (corresponding to 13.28 mmol) of 2-(4'-hydroxyphenyl)-6-hydroxyimidazo[1,2-a]pyridine (FIG. 5, Step 6).

560 mg (corresponding to 2.48 mmol) of 2-(4'-hydroxyphenyl)-6-hydroxyimidazo[1,2-a]pyridine was dissolved in 21 mL of N,N-dimethylformamide, and 1.37 g (corresponding to 9.90 mmol) of potassium carbonate and 349 mg (corresponding to 2.48 mmol) of 1-bromo-3-fluoropropane were added thereto. The solution was stirred at room temperature for 24 hours. The reaction solution was concentrated under reduced pressure, and then supplemented with 10 mL of chloroform and 10 mL of methanol to obtain slurry. The slurry was filtered and filtrate was concentrated. The resulting crude product was purified by silica gel column chromatography (elution solvent: chloroform/methanol=20/1), to obtain 151 mg (corresponding to 0.527 μmol) of 6-(3'-fluoropropoxy)-2-(4'-hydroxyphenyl)imidazo[1,2-a]pyridine (FIG. 5, Step 7).

The NMR measurement results of the resulting 6-(3'-fluoropropoxy)-2-(4'-hydroxyphenyl)imidazo[1,2-a]pyridine (internal standard: dimethylsulfoxide) are shown below.

NMR apparatus employed: JNM-GSX-270 (manufactured by Japan Electron Optics Laboratory Co., Ltd. (JEOL))

$^1$H-NMR (solvent: dimethylsulfoxide-d6; resonance frequency: 270 MHz): δ 9.52 (s, 1H), 8.22 (d, J=2.2 Hz, 1H), 8.08 (s, 1H), 7.75-7.65 (m, 2H), 7.44 (d, J=9.6 Hz, 1H), 6.99 (dd, J=9.6, 2.2 Hz, 1H), 6.85-6.75 (m, 2H), 4.62 (dt, $^2J_{HF}$=47.0 Hz, J=6.0 Hz, 2H), 4.05 (t, J=6.0 Hz, 2H), 2.13 (dquint, $^3J_{HF}$=25.9 Hz, J=6.0 Hz, 2H).

Example I-8

Synthesis of 6-bromo-2-(4'-hydroxyphenyl)imidazo [1,2-a]pyrimidine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 6, Step 1).

748 mg (corresponding to 3.5 mmol) of 2-bromo-4'-hydroxyacetophenone and 605 mg (corresponding to 3.5 mmol) of 2-amino-5-bromopyrimidine were dissolved in 30 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 15 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure. The resulting crude product was recrystallized from N,N-dimethylformamide, to obtain 289 mg (corresponding to 0.997 mmol) of 6-bromo-2-(4'-hydroxyphenyl)imidazo[1, 2-a]pyrimidine (FIG. 6, Step 2).

The NMR measurement results of the resulting 6-bromo-2-(4'-hydroxyphenyl)imidazo[1,2-a]pyrimidine (internal standard: dimethylsulfoxide) are shown below.

NMR apparatus employed: JNM-ECP-500 (manufactured by Japan Electron Optics Laboratory Co., Ltd. (JEOL))

$^1$H-NMR (solvent: dimethylsulfoxide-d6, resonance frequency: 500 MHz): δ 9.56 (br. s, 1H), 9.21 (d, J=2.5 Hz, 1H), 8.46 (d, J=2.5 Hz, 1H), 8.09 (s, 1H), 7.79-7.75 (m, 2H), 6.83-6.79 (m, 2H).

$^{13}$C-NMR (solvent: dimethylsulfoxide-d6, resonance frequency: 125 MHz): δ 158.63, 149.99, 147.68, 146.88, 134.78, 127.93, 124.52, 116.23, 106.83, 103.94.

Example I-9

Synthesis of 6-fluoro-2-(4'-hydroxyphenyl)imidazo [1,2-a]pyridine 70 mL of ethyl acetate was added to 40.0 g (corresponding to 179 mmol) of cupric bromide to obtain a suspension, to which a solution of 11.6 g (corresponding to 85.3 mmol) of 4'-hydroxyacetophenone in a mixed solution of 70 mL of ethyl acetate and 70 mL of chloroform was added. Then, the resulting mixture was refluxed. After 5.5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 10.2 g (corresponding to 47.3 mmol) of 2-bromo-4'-hydroxyacetophenone (FIG. 7, Step 1).

439 mg (corresponding to 2.0 mmol) of 2-bromo-4'-hydroxyacetophenone and 224 mg (corresponding to 2.0 mmol) of 2-amino-5-fluoropyridine were dissolved in 20 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 8 mL of water and 8 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 302 mg (corresponding to 1.32 mmol) of 6-fluoro-2-(4'-hydroxyphenyl)imidazo[1,2-a]pyridine (FIG. 7, Step 2).

The NMR measurement results of the resulting 6-fluoro-2-(4'-hydroxyphenyl)imidazo[1,2-a]pyridine (internal standard: dimethylsulfoxide) are shown below.

NMR apparatus employed: JNM-ECP-500 (manufactured by Japan Electron Optics Laboratory Co., Ltd. (JEOL))

$^1$H-NMR (solvent: dimethylsulfoxide-d6, resonance frequency: 500 MHz): δ 9.45 (br. s, 1H), 8.65 (ddd, $^3J_{HF}$=4.6 Hz, J=2.5, 0.7 Hz, 1H), 8.16-8.15 (m, 1H), 7.75-7.69 (m, 2H), 7.56-7.51 (m, 1H), 7.23 (ddd, $^3J_{HF}$=8.4 Hz, J=9.9, 2.5 Hz, 1H), 6.82-6.76 (m, 2H).

$^{13}$C-NMR (solvent: dimethylsulfoxide-d6, resonance frequency: 125 MHz): δ 157.82, 152.81 (d, $^1J_{CF}$=232.3 Hz), 146.58, 142.92, 127.35, 124.99, 117.19 (d, $^3J_{CF}$=9.6 Hz), 116.40 (d, $^2J_{CF}$=25.9 Hz), 115.89, 113.66 (d, $^2JC_F$=41.8 Hz), 109.48.

$^{19}$F-NMR (solvent: dimethylsulfoxide-d6, resonance frequency: 470 MHz): δ 141.93 (br. s).

Example I-10

Synthesis of 2-(4'-hydroxyphenyl)-6-nitroimidazo[1, 2-a]pyridine 70 mL of ethyl acetate was added to 40.0 g (corresponding to 179 mmol) of cupric bromide to obtain a suspension, to which a solution of 11.6 g (corresponding to 85.3 mmol) of 4'-hydroxyacetophenone in a mixed solution of 70 mL of ethyl acetate and 70 mL of chloroform was added. Then, the resulting mixture was refluxed. After 5.5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 10.2 g (corresponding to 47.3 mmol) of 2-bromo-4'-hydroxyacetophenone (FIG. 8, Step 1).

432 mg (corresponding to 2.0 mmol) of 2-bromo-4'-hydroxyacetophenone and 279 mg (corresponding to 2.0 mmol) of 2-amino-5-nitropyridine were dissolved in 20 mL of acetonitrile. The resulting solution was refluxed in an oil bath at 110° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 8 mL of water and 8 mL of methanol. Then, about 8 mL of a saturated sodium hydrogencarbonate solution was added thereto, and the mixture was sonicated for 3 minutes using an ultrasonic washing machine. Precipitates were filtered and recovered from the resulting mixture, sufficiently washed with water, and dried under reduced pressure, to obtain 148 mg (corresponding to 0.580 mmol) of 2-(4'-hydroxyphenyl)-6-nitroimidazo[1,2-a]pyridine (FIG. 8, Step 2).

The NMR measurement results of the resulting 2-(4'-hydroxyphenyl)-6-nitroimidazo[1,2-a]pyridine (internal standard: dimethylsulfoxide) are shown below.

NMR apparatus employed: JNM-ECP-500 (manufactured by Japan Electron Optics Laboratory Co., Ltd. (JEOL))

$^1$H-NMR (solvent: dimethylsulfoxide-d6, resonance frequency: 500 MHz): δ 9.74-9.72 (m, 1H), 9.59 (br. s, 1H), 8.39 (s, 1H), 7.87 (dd, J=9.9, 2.3 Hz, 1H), 7.79-7.74 (m, 2H), 7.65-7.61 (m, 1H), 6.84-6.80 (m, 2H).

$^{13}$C-NMR (solvent: dimethylsulfoxide-d6, resonance frequency: 125 MHz): δ 158.47, 148.51, 145.25, 136.63, 127.93, 127.81, 124.06, 118.92, 116.09, 115.92, 110.37.

Example II-1

Synthesis of 6-tributylstannyl-2-(4'-hydroxyphenyl)imidazo[1,2-a]pyrimidine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction solution was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 10, Step 1).

748 mg (corresponding to 3.48 mmol) of 2-bromo-4'-hydroxyacetophenone and 605 mg (corresponding to 3.48 mmol) of 5-bromo-2-aminopyrimidine were dissolved in 30 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 15 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure. The obtained solid was recrystallized from N,N-dimethylformamide, to obtain 289 mg (corresponding to 1.00 mmol) of 6-bromo-2-(4'-hydroxyphenyl)imidazo[1,2-a]pyrimidine (FIG. 10, Step 2).

75.4 mg (corresponding to 0.260 mmol) of 6-bromo-2-(4'-hydroxyphenyl)imidazo[1,2-a]pyrimidine was dissolved in 10.0 mL of dioxane, and 2.0 mL of triethylamine was added thereto. Then, 0.20 mL (corresponding to 0.39 mmol) of bis(tributyltin) and 20.1 mg (at a catalytic amount) of tetrakistriphenylphosphine palladium were added thereto. After the reaction mixture was stirred at 90° C. for 10 hours, the solvent was distilled off under reduced pressure. The residue was purified by flash silica gel column chromatography (elution solvent: hexane/ethyl acetate=1/1), to obtain 24.0 mg (corresponding to 0.048 mmol) of 6-tributylstannyl-2-(4'-hydroxyphenyl)imidazo[1,2-a]pyrimidine (FIG. 10, Step 3).

The NMR measurement results of the resulting 6-tributylstannyl-2-(4'-hydroxyphenyl)imidazo[1,2-a]pyrimidine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.41 (s, 1H), 8.23 (s, 1H), 7.80 (d, J=8.7 Hz, 2H), 7.63 (s, 1H), 6.93 (d, J=8.7 Hz, 2H), 1.57-1.51 (m, 6H), 1.37-1.23 (m, 6H), 1.16-1.12 (m, 6H), 0.88 (d, J=7.3 Hz, 9H)

Example II-2

Synthesis of 6-tributylstannyl-2-(4'-hydroxyphenyl)imidazo[1,2-a]pyrazine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction solution was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 11, Step 1).

4.66 g (corresponding to 21.6 mmol) of 2-bromo-4'-hydroxyacetophenone and 2.53 g (corresponding to 14.5 mmol) of 5-bromo-2-aminopyrazine were dissolved in 100 mL of acetonitrile. The resulting solution was refluxed in an oil bath at 110° C. for 3.5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 20 mL of a saturated sodium hydrogencarbonate solution was added thereto, and the mixture was sonicated for 10 minutes using an ultrasonic washing machine. Precipitates were filtered and recovered from the resulting mixture, sufficiently washed with water, and dried under reduced pressure, to obtain 1.32 g (corresponding to 4.55 mmol) of 6-bromo-2-(4'-hydroxyphenyl)imidazo[1,2-a]pyrazine (FIG. 11, Step 2).

1.00 g (corresponding to 3.45 mmol) of 6-bromo-2-(4'-hydroxyphenyl)imidazo[1,2-a]pyrazine was dissolved in 50.0 mL of dioxane, and 20.0 mL of triethylamine was added thereto. Then, 4.5 mL (corresponding to 5.18 mmol) of bis(tributyltin) and 239 mg (at a catalytic amount) of tetrakistriphenylphosphine palladium were added thereto. After the reaction mixture was stirred at 90° C. for 24 hours, the solvent was distilled off under reduced pressure. The residue was purified by flash silica gel column chromatography (elution solvent: hexane/ethyl acetate=1/1), to obtain 314 mg (corresponding to 0.628 mmol) of 6-tributylstannyl-2-(4'-hydroxyphenyl)imidazo[1,2-a]pyrazine (FIG. 11, Step 3).

The NMR measurement results of the resulting 6-tributylstannyl-2-(4'-hydroxyphenyl)imidazo[1,2-a]pyrazine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 9.21 (s, 1H), 7.95 (s, 1H), 7.79 (d, J=8.7 Hz, 2H), 7.77 (s, 1H), 6.91 (d, J=8.7 Hz, 2H), 1.70-1.55 (m, 6H), 1.38-1.31 (m, 6H), 1.18-1.15 (m, 6H), 0.89 (d, J=7.3 Hz, 9H)

$^{13}$C-NMR (solvent: chloroform-dl, resonance frequency: 500 MHz): δ 157.3, 146.4, 143.5, 140.3 128.0, 124.9, 123.6, 116.1, 106.9, 29.0, 27.3, 13.7, 10.0.

Example II-3

Synthesis of 2-(4'-hydroxyphenyl)-6-iodoimidazo[1,2-a]pyrazine 314 mg (corresponding to 0.628 mmol) of 6-tributylstannyl-2-[4'-hydroxyphenyl]imidazo[1,2-a]pyrazine obtained from Example II-2 was dissolved in 5.0 mL of dichloromethane, to which 114 mg (corresponding to 0.942 mmol) of iodine dissolved in 5.0 mL of dichloromethane was added. The reaction mixture was stirred at the temperature of 0° C. for 10 minutes and at room temperature for 30 hours. Then, a saturated aqueous sodium hydrogencarbonate solution and a saturated aqueous sodium thiosulfate solution were added thereto. Precipitates were filtered and recovered, washed with water and ethyl acetate in this order, and dried under reduced pressure, to obtain 131 mg (corresponding to 0.389 mmol) of 2-(4'-hydroxyphenyl)-6-iodoimidazo[1,2-a]pyrazine (FIG. 12, Step 1).

The NMR measurement results of the resulting 2-(4'-hydroxyphenyl)-6-iodoimidazo[1,2-a]pyrazine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: dimethylformamide-d7, resonance frequency: 500 MHz): δ 9.89 (s, 1H), 9.01 (s, 1H), 8.82 (s, 1H), 8.42 (s, 1H), 7.92 (d, J=8.7 Hz, 2H), 6.93 (d, J=8.7 Hz, 2H).

Example II-4

Synthesis of 8-tributylstannyl-2-(4'-hydroxyphenyl)imidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction solution was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 13, Step 1).

432 mg (corresponding to 2.01 mmol) of 2-bromo-4'-hydroxyacetophenone and 348 mg (corresponding to 2.01 mmol) of 3-bromo-2-aminopyridine were dissolved in 20 mL of acetonitrile. The resulting solution was refluxed in an oil bath at 110° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 8 mL of water and 8 mL of methanol. Then, about 8 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 368 mg (corresponding to 1.27 mmol) of 8-bromo-2-(4'-hydroxyphenyl)imidazo[1,2-a]pyridine (FIG. 13, Step 2).

75.2 mg (corresponding to 0.260 mmol) of 8-bromo-2-(4'-hydroxyphenyl)imidazo[1,2-a]pyridine was dissolved in 10.0 mL of dioxane, and 2.0 mL of triethylamine was added thereto. Then, 0.20 mL (corresponding to 0.39 mmol) of bis(tributyltin) and 20.1 mg (at a catalytic amount) of tetrakistriphenylphosphine palladium were added thereto. After the reaction mixture was stirred at 90° C. for 11 hours, a solvent was distilled off under reduced pressure. The residue was purified by flash silica gel column chromatography (elution solvent: hexane/ethyl acetate=1/1), to obtain 62.5 mg (corresponding to 0.125 mmol) of 8-tributylstannyl-2-(4'-hydroxyphenyl)imidazo[1,2-a]pyridine (FIG. 13, Step 3).

The NMR measurement results of the resulting 8-tributylstannyl-2-(4'-hydroxyphenyl)imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.01 (d, J=6.4 Hz, 1H), 7.87 (d, J=8.7 Hz, 2H), 7.70 (s, 1H), 7.17 (d, J=6.4 Hz, 1H), 6.87 (d, J=8.7 Hz, 2H), 6.68-6.66 (m, 1H), 1.69-1.56 (m, 6H), 1.38-1.30 (m, 6H), 1.28-1.16 (m, 6H), 0.88 (t, J=7.3 Hz, 9H)

$^{13}$C-NMR (solvent: chloroform-dl, resonance frequency: 500 MHz): δ 145.2, 141.0, 139.2, 132.4, 131.8, 127.7, 127.3, 125.0, 115.4, 112.2, 106.4, 29.2, 27.4, 13.7, 10.2.

Example II-5

Synthesis of [$^{123}$I]-2-(4'-hydroxyphenyl)-6-iodoimidazo[1,2-a]pyrimidine

To 100 µL of a solution of 6-tributylstannyl-2-(4'-hydroxyphenyl)imidazo[1,2-a]pyrimidine in methanol (at a concentration of 1 mg/mL), 100 µL of 2 mol/L hydrochloric acid, [$^{123}$I]sodium iodide of 621 MBq (150 µL in volume), 20 µL of 1 mmol/L sodium iodide solution and 20 µL of 10% (w/v) hydrogen peroxide were added. After the mixed solution was heated at 50° C. for 10 minutes, the solution was subjected to HPLC under the same conditions as described in Example I-2, to obtain [$^{123}$I]-2-(4'-hydroxyphenyl)-6-iodoimidazo[1,2-a]pyrimidine as a fraction.

The same operation as the preceding paragraph was performed to obtain [$^{123}$I]-2-(4'-hydroxyphenyl)-6-iodoimidazo[1,2-a]pyrimidine (the amount of reagents to be added: 150 µL of a solution of 6-tributylstannyl-2-(4'-hydroxyphenyl)-6-iodoimidazo[1,2-a]pyrimidine in methanol (concentration: 1 mg/mL), 75 µL of 2 mol/L hydrochloric acid, [$^{123}$I]sodium iodide of 487 MBq (150 µL in volume), 20 µL of 1 mmol/L sodium iodide solution and 30 µL of 10% (w/v) hydrogen peroxide).

Two fractions obtained by the operations of the two preceding paragraphs were mixed, and 10 ml of water was added thereto. The resulting solution was passed through a reversed phase column (trade name: Sep-Pak (registered trademark, Waters Investments Limited) Light C8 Cartridges manufactured by Waters: the packed amount of the packing agent: 130 mg) so that the column adsorbs and collects [$^{123}$I]-2-(4'-hydroxyphenyl)-6-iodoimidazo[1,2-a]pyrimidine. The column was rinsed with 1 mL of water, and then 1 mL of diethylether was passed therethrough to elute [$^{123}$I](4'-hydroxyphenyl)-6-iodoimidazo[1,2-a]pyridine. The amount of radioactivity of the obtained compound was 67 MBq at the end of synthesis. Further, the TLC analysis was conducted under the following conditions, and as a result, the radiochemical purity of the compound was 92.5%.

TLC Analysis Conditions:
TLC plate: Silica Gel 60 F$_{254}$ (trade name; manufactured by Merck & Co., Inc.)
Mobile phase: chloroform/methanol/triethylamine=100/1/2
Detector: Rita Star (trade name; manufactured by raytest)

Example II-6

Synthesis of [$^{123}$I]-2-(4'-hydroxyphenyl)-6-iodoimidazo[1,3]pyrazine

To 100 µL of a solution of 6-tributylstannyl-2-(4'-hydroxyphenyl)imidazo[1,2-a]pyrazine in methanol (concentration: 1 mg/mL), 75 µL of 2 mol/L hydrochloric acid, [$^{123}$I]sodium iodide of 469 MBq (100 µL in volume), 20 µL of 1 mmol/L sodium iodide solution and 20 µL of 10% (w/v) hydrogen peroxide were added. After the mixed solution was heated at 50° C. for 10 minutes, the solution was subjected to HPLC under the same conditions as described in Example I-2, to obtain [$^{123}$I]-2-(4'-hydroxyphenyl)-6-iodoimidazo[1,3]pyrazine as a fraction.

10 ml of water was added to the fraction. The resulting solution was passed through a reversed phase column (trade name: Sep-Pak (registered trademark, Waters Investments Limited) Light C8 Cartridges manufactured by Waters: the packed amount of the packing agent: 130 mg) so that the column adsorbs and collects [$^{123}$I]-2-(4'-hydroxyphenyl)-6-iodoimidazo[1,2-a]pyrazine. The column was rinsed with 1 mL of water, and then 1 mL of diethyl ether was passed therethrough to elute [$^{123}$I]-2-(4'-hydroxyphenyl)-6-iodoimidazo[1,2-a]pyrazine. The amount of radioactivity of the obtained compound was 133 MBq at the end of synthesis. Further, the TLC analysis was conducted under the same conditions as described in Example II-5, and as a result, the radiochemical purity of the compound was 99.0%.

Example II-7

Synthesis of [$^{123}$I]-2-(4'-hydroxyphenyl)-8-iodoimidazo[1,2-a]pyridine

To 70 µL of a solution of 8-tributylstannyl-2-(4'-hydroxyphenyl)imidazo[1,2-a]pyrazine in methanol (concentration: 1 mg/mL), 50 µL of 2 mol/L hydrochloric acid, [$^{123}$I]sodium iodide of 454 MBq (100 µL in volume), 20 µL of 1 mmol/L sodium iodide solution and 20 µL of 10% (w/v) hydrogen peroxide were added. After the mixed solution was heated at 50° C. for 10 minutes, the solution was subjected to HPLC under the same conditions as described in Example I-2, to obtain [$^{123}$I]-2-(4'-hydroxyphenyl)-8-iodoimidazo[1,2-a]pyridine as a fraction.

10 ml of water was added to the fraction. The resulting solution was passed through a reversed phase column (trade name: Sep-Pak (registered trademark, Waters Investments Limited) Light C18 Cartridges manufactured by Waters: the packed amount of the packing agent: 130 mg) so that the column adsorbs and collects [$^{123}$I]-2-(4'-hydroxyphenyl)-8-iodoimidazo[1,2-a]pyridine. The column was rinsed with 1 mL of water, and then 1 mL of diethyl ether was passed therethrough to elute hydroxyphenyl)-8-iodoimidazo[1,2-a]pyridine. The amount of radioactivity of the obtained compound was 185 MBq at the end of synthesis. Further, the TLC analysis was conducted under the same conditions as described in Example II-5, and as a result, the radiochemical purity of the compound was 91.7%.

Reference Example 1

Synthesis of [$^{125}$I]-IMPY

[$^{125}$I]-IMPY was prepared in accordance with the following steps for use in Comparative Example (Comparative Example I-6) for evaluation on logP$_{octanol}$.

In accordance with the literature (Zhi-Ping Zhuang et al., J. Med. Chem, 2003, 46, p. 237-243), 6-tributylstannyl-2-[4'-(N,N-dimethylamino)phenyl]imidazo[1,2-a]pyridine was synthesized, and dissolved in methanol (concentration: 1 mg/mL). To 53 µL of the resulting solution, 75 µL of 1 mol/L hydrochloric acid, 20 µL of [$^{125}$I]sodium iodide of 13.5 MBq, and 10 µL of 10% (w/v) hydrogen peroxide were added. After the mixed solution was left to stand at 50° C. for 10 minutes, the solution was subjected to HPLC under the same conditions as described in Example I-2, to obtain [$^{125}$I]-IMPY fraction.

10 ml of water was added to the fraction. The resulting solution was passed through a reversed phase column (trade name: Sep-Pak (registered trademark, Waters Investments Limited) Light C18 Cartridges manufactured by Waters; the packed amount of the packing agent: 130 mg), so that the column adsorbs and collects the [$^{125}$I]-IMPY. The column was rinsed with 1 mL of water, and then 1 mL of ethanol was passed therethrough, to elute [$^{125}$I]-IMPY. The obtained radioactivity was 2.6 MBq at the end of synthesis. Further, the TLC analysis was conducted under the same conditions as described in Example I-2, and as a result, the radiochemical purity of the compound was 98.0%.

Reference Example 2

Synthesis of [$^{123}$I]-IMPY

[$^{123}$I]-IMPY was prepared in accordance with the following steps for use in Comparative Examples (Comparative Example I-7) for evaluations on accumulation in brain.

In accordance with the literature (Zhi-Ping Zhuang et al., J. Med. Chem, 2003, 46, p. 237-243), 6-tributylstannyl-2-[4'-(N,N-dimethylamino)phenyl]imidazo[1,2-a]pyridine was synthesized, and dissolved in methanol (concentration: 1 mg/mL). To 53 μL of the resulting solution, 100 μL of 1 mol/L hydrochloric acid, 20-50 μL of [$^{123}$I]sodium iodide of 190-240 MBq, 10 μL of a 1 mmol/L sodium iodide solution and 10 μL of 10% (w/v) hydrogen peroxide were added. After the mixed solution was left to stand at 50° C. for 10 minutes, the solution was subjected to HPLC under the same conditions as described in Example I-2, to obtain [$^{123}$I]-IMPY fraction.

10 ml of water was added to the fraction. The resulting solution was passed through a reversed phase column (trade name: Sep-Pak (registered trademark, Waters Investments Limited) Light C18 Cartridges manufactured by Waters; the packed amount of the packing agent: 130 mg), so that the column adsorbs and collects the [$^{123}$I]-IMPY. The column was rinsed with 1 mL of water, and then 1 mL of ethanol was passed therethrough, to elute [$^{123}$I]-IMPY. The obtained radioactivity was 47-56 MBq at the end of synthesis. Further, the TLC analysis was conducted under the same conditions as described in Example I-2, and as a result, the radiochemical purity of the compound was 98.0%.

Examples I-11 to I-14, Comparative Examples I-1 to I-5

Measurement of Amyloid Affinity

Affinity of the present compounds with amyloid was examined by the following in vitro binding tests.

(1) Aβ$_{1-40}$ (Peptide Institute, INC.) was dissolved in phosphate buffer (pH 7.4) and shaken at 37° C. for 62-72 hours, to obtain a suspension of aggregated Aβ (concentration: 1 mg/mL equivalent, hereinafter referred to as amyloid suspension in these Examples).

(2) According to the method described in a literature (Naiki, H., et al., Laboratory Investigation 74, p. 374-383 (1996)), the amyloid suspension was subjected to qualitative experiment based on fluorescence spectrophotometric method using Thioflavin T (manufactured by Fluka) to confirm that the aggregated Aβ obtained in (1) was amyloid (measurement conditions: excitation wavelength of 446 nm, and emission wavelength of 490 nm).

(3) According to the method described in a literature (Wang, Y., et al., J. Labeled Compounds Radiopharmaceut. 44, S239 (2001)), [$^{125}$I]2-(3'-iodo-4'-aminophenyl)benzothiazole (hereinafter referred to as [$^{125}$I]3'-I-BTA-O) was prepared from a labeling precursor 2-(4'-aminophenyl)benzothiazole, and dissolved in ethanol. [$^{125}$I]sodium iodide of 12-71 MBq (10-30 μL in volume) was used for the production, to obtain [$^{125}$I]3'-I-BTA-0 of 1-22 MBq at the end of synthesis. As Congo Red, Thioflavin T and 6-methyl-2-[4'-(N,N-dimethylamino)phenyl]benzothiazole (hereinafter referred to as 6-Me-BTA-2), commercially available reagents were weighed and used as they were.

(4) 2-(3'-Iodo-4'-aminophenyl)benzothiazole (hereinafter referred to as 3'-I-BTA-O) and IMPY were synthesized according to the methods described in a literature (Wang. Y., et al., J. Labelled Compounds Radiopharmaceut. 44, S239 (2001)) and a literature (Zhuang, Z. P., et al., J. Med. Chem. 46, 237 (2003)) respectively.

(5) Samples in which [$^{125}$I]3'-I-BTA-0, each compound for evaluation and amyloid were dissolved in a 0.1% bovine serum albumin-containing phosphate buffer (pH 7.4) at final concentrations shown in Table 2 were prepared. The resulting samples were placed in each well (about 0.3 mL in volume) of a 96-well microplate.

TABLE 2

Final concentrations of each compound in sample solutions

| Experiment | Compound for evaluation | Concentration of compound for evaluation | [$^{125}$I]3'-I-BTA-0 concentration | Amyloid |
|---|---|---|---|---|
| Comparative Example I-1 | 3'-I-BTA-0 | Each concentration of 0, 0.001, 0.01, 0.1, 1, 10, 100, 1000 nmol/L | 400 pmol/L | 1 μmol/L |
| Comparative Example I-2 | Congo Red | | | |
| Comparative Example I-3 | Thioflavin T | | | |
| Comparative Example I-4 | 6-Me-BTA-2 | | | |
| Comparative Example I-5 | IMPY | | | |
| Example I-11 | Compound 1 | | | |
| Example I-12 | Compound 2 | | | |
| Example I-13 | Compound 3 | | | |
| Example I-14 | Compound 4 | | | |

(6) The microplate filled with the sample solutions was shaken at a given rate (400 rpm) at 22° C. for 3 hours. Then, each sample solution was filtered through a glass fiber filter (trade name: Mulutiscreen™-FC, manufactured by Millipore), to separate the [$^{125}$I]3'-I-BTA-0 attached to amyloid from the [$^{125}$I]3'-I-BTA-0 free from amyloid.

(7) The glass fiber filter used for the filtration of each sample solution was washed with a 0.1% bovine serum albumin-containing phosphate buffer (pH 7.4) (0.5 mL×5), and radioactivity of the glass fiber filter was measured with an autowell gamma system (manufactured by Aloka, Type: ARC-301B). The radioactivity was used as the radioactivity level of each sample solution attached to amyloid for calculating an inhibition ratio (hereinafter, A denotes the radioactivity level in a sample with zero (0) concentration of each compound for evaluation, and B denotes the radioactivity level in a sample with 0.001 nmol/L or higher concentration of each compound for evaluation).

(8) Separately, a solution containing 15 μmol/L of 6-Me-BTA-2, 400 pmol/L of [$^{125}$I]3'-I-BTA-0 and 1 μmol/L of Aβ$_{1-40}$ in a 0.1% bovine serum albumin-containing phosphate buffer (pH 7.4) was prepared and subjected to the same procedures as described above in (6) and (7) to measure a radioactivity level. The measured radioactivity level was defined as the background radioactivity level, and used in the calculation of the inhibition ratio (hereinafter referred to as BG).

(9) Using the radioactivity levels measured above in (7) and (8), the inhibition ratio was determined by the following formula (1).

$$\text{Inhibition Ratio} = \frac{B - BG}{A - BG} \times 100 \ (\%) \qquad (1)$$

A graph in which values converted by probit transformation from the obtained inhibition ratios were plotted relative to logarithms of concentrations of compounds for evaluation was prepared to obtain an approximate straight line by the least square method. Using the line, the concentration of each compound for evaluation was determined, at which the radioactivity level is half of the level of the sample free from each compound for evaluation, and was defined as a 50% inhibition concentration of each compound (hereinafter referred to as $IC_{50}$% value). Using the value as an indicator, affinity of each compound for evaluation with amyloid (aggregated $A\beta_{1-40}$) was evaluated.

$IC_{50}$% value of each compound for evaluation is shown in Table 3. Compounds 1 to 4 all showed $IC_{50}$% values of less than 100 and had higher affinity with amyloid (aggregated $A\beta_{1-40}$) than Congo Red and Thioflavin T. The results show that Compounds 1 to 4 have good affinity with amyloid (aggregated $A\beta_{1-40}$). In particular, Compound 1 had higher affinity with amyloid (aggregated $A\beta_{1-40}$) than 3'-I-BTA-O and 6-Me-BTA-2 and had the affinity comparable to IMPY.

TABLE 3

$IC_{50\%}$ values of the present compounds

| Experiment | Compound for evaluation | $IC_{50\%}$ values (nmol/L) |
| --- | --- | --- |
| Comparative Example I-1 | 3'-I-BTA-0 | 10.1 |
| Comparative Example I-2 | Congo Red | >1000 |
| Comparative Example I-3 | Thioflavin T | >1000 |
| Comparative Example I-4 | 6-Me-BTA-2 | 25.4 |
| Comparative Example I-5 | IMPY | 4.0 |
| Example I-11 | Compound 1 | 4.4 |
| Example I-12 | Compound 2 | 46.0 |
| Example I-13 | Compound 3 | 54.4 |
| Example I-14 | Compound 4 | 54.1 |

Example I-15, Example II-8 to II-10, Comparative Example I-6

Measurement of Partition Coefficient Based on the Octanol Extraction Method

Partition coefficients based on the octanol extraction method (hereinafter referred to as $\log P_{octanol}$) were measured, which are generally known as an indicator of permeability of compounds through the blood-brain barrier (hereinafter referred to as BBB).

A diethyl ether solution of Compound 5 prepared in Example I-2 (Example I-15), a diethyl ether solution of Compound 9 prepared in Example II-5 (Example II-8), a diethyl ether solution of Compound 10 prepared in Example II-6 (Example II-9), a diethyl ether solution of Compound 11 prepared in Example II-7 (Example II-10) and a diethyl ether solution of [$^{123}$I]-IMPY prepared in Reference Example 1 (Comparative Example I-6) were each diluted with 10 mg/mL ascorbic acid-containing physiological saline solution, and adjusted to radioactive concentration of 20-30 MBq/mL. 10 μL each of the prepared sample solution was respectively added to 2 mL of octanol, further, 2 mL of 10 mmol/L phosphate buffer (pH 7.4) was added, and stirred for 30 seconds. After the mixture was centrifuged with a low-speed centrifuge (2000 rpm×60 min.), the octanol layer and the water layer were sampled each in an amount of 1 mL, and subjected to measurement of radioactivity count with an autowell gamma system (Type: ARC-301B, manufactured by Aloka). Using the obtained radioactivity count, $\log P_{octanol}$ was calculated in accordance with the equation (2).

$$\log P_{octanol} = \log_{10}\left(\frac{\text{Radioactivity count of octanol layer}}{\text{Radioactivity count of water later}}\right) \qquad (2)$$

The results are shown in Table 4. Compound 5 showed a $\log P_{octanol}$ value of 1.6, and [$^{125}$I]-IMPY showed a $\log P_{octanol}$ value of 2.1. It is known that compounds permeable to BBB show a $\log P_{octanol}$ value between 1 and 3 (Douglas D. Dischino et al., J. Nucl. Med., (1983), 24, p. 1030-1038). Thus, it is implied that both compounds have a BBB permeability comparable to IMPY.

TABLE 4

$\log P_{octanol}$ value of the present compound

| Experiment | Compound | $\log P_{octanol}$ value |
| --- | --- | --- |
| Comparative Example I-6 | [$^{125}$I]-IMPY | 2.1 |
| Example I-15 | Compound 5 | 1.6 |
| Example II-8 | Compound 9 | 1.7 |
| Example II-9 | Compound 10 | 2.3 |
| Example II-10 | Compound 11 | 3.0 |

Example I-16, Comparative Example I-7

Measurement of Transferability into Brain and Clearance

Using Compound 6, a time course change of radioactive accumulation in brain of male Wistar rats (7-week old) was measured.

0.05 mL (20-30 MBq/mL in radioactive concentration) of a solution of Compound 6 (Example I-16) in a 10 mg/mL ascorbic acid-containing physiological saline solution and 0.05 mL (20-30 MBq/mL in radioactive concentration) of a solution of [$^{123}$I]-IMPY (Comparative Example I-7) prepared above in Reference Example 2 in a 10 mg/mL ascorbic acid-containing physiological saline solution were injected under thiopental anesthesia into the tail vein of respective Wistar rats (7-week old). The rats were sacrificed by bleeding from abdominal artery, and brains were removed and subjected to measurement of radioactivity (hereinafter referred to as A in this Example) with an autowell gamma system (Type: ARC-301B, manufactured by Aloka) and further subjected to measurement of mass of brains 2, 5, 30 and 60 minutes after the injection. Also, radioactivity (hereinafter referred to as B in this Example) of 0.05 mL of a 1000-fold diluted solution of the injected solution was measured in the same manner as above. Using these measurement results, radioactive accumulation per unit weight of brain (% ID/g) at the respective time points was calculated in accordance with the following formula (5).

Two animals were used for both Example I-16 and Comparative Example I-7 at the respective time points.

$$\%\,ID/g = \frac{A}{B \times 1000 \times \text{brain weight}} \times 100 \quad (5)$$

The results are shown in Table 5. As shown in Table 5, Compound 6 showed a accumulation comparable to $^{123}$I-IMPY at the time point of two minutes after the injection, and then showed a tendency to rapidly clear away in 60 minutes. These results suggest that Compound 6 possesses excellent transferability to brain and rapid clearance from brain like $^{123}$I-IMPY.

TABLE 5

Radioactive accumulation in brain of Compound 6 after intravenous injection (rats)

| | | Radioactive accumulation per unit weight (% ID/g) | | | |
|---|---|---|---|---|---|
| | Compound | After 2 min. | After 5 min. | After 30 min. | After 60 min. |
| Comparative Example I-7 | $^{123}$I-IMPY | 1.02 | 0.99 | 0.20 | 0.08 |
| Example I-16 | Compound 6 | 0.96 | 0.69 | 0.16 | 0.04 |

Example I-17

Confirmation of Imaging of Amyloid in Brain

The following experiment was carried out in order to examine whether amyloid in brain can be imaged by the compound of the present invention.

(1) Aβ$_{1-40}$ (manufactured by Peptide Institute, INC.) was dissolved in phosphate buffer (pH 7.4) and shaken at 37° C. for 72 hours, to obtain a suspension of aggregated Aβ (Aβ concentration: 1 mg/mL equivalent, hereinafter referred to as amyloid suspension in this Example).

(2) 25 μL (corresponding to 25 μg) of the amyloid suspension was injected into an amygdaloid nucleus on one side of a male Wistar rat (7-week old). As a control, 25 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) Compound 6 was dissolved in a 10 mg/mL ascorbic acid-containing physiological saline solution to obtain a sample solution (32 MBq/mL in radioactivity concentration). This solution was injected into the rat through the tail vein (dosage: 0.5 mL, dosed radioactivity: 16 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (type: TE2000-U model; manufactured by NIKON Corporation; excitation wavelength: 400-440 nm; detection wavelength: 470 nm). Thus, it was confirmed that amyloid was deposited on the slice (FIG. 9b).

FIG. 9 shows images by autoradiogram and Thioflavin T staining of the brain slice of the rat to which amyloid was injected intracerebrally. As shown in FIG. 9, a marked accumulation of radioactivity was observed in the amygdaloid nucleus on the side to which the amyloid suspension was injected. From the result of Thioflavin T staining in the site where radioactivity accumulated, it was confirmed that amyloid was present in the accumulation site. On the other hand, no significant accumulation of radioactivity was observed in the amygdaloid nucleus on the side to which the physiological saline solution was injected, compared with the other sites.

These results suggest that Compound 6 possesses a property of accumulating on intracerebral amyloid, and a capability of imaging intracerebral amyloid.

Example I-18 to I-20

Reverse Mutation Test

In order to examine mutagenicity of Compounds 1, 2 and 4, reverse mutation test using *Salmonella typhimurium* TA98 and TA100 (hereinafter referred to as Ames test) was conducted.

The test was conducted without addition of S9mix and with addition of S9mix. Dimethylsulfoxide was used as a negative control. A positive control was 2-(2-furyl)-3-(5-nitro-2-furyl)acrylamide in case S9mix was not added, and 2-aminoanthracene in case S9 mix was added.

The amount of each sample to be added to the test plate was 7 dosages (geometric ratio 4) with the maximum dose being 5000 μg/plate. After a sample to be examined and a strain (TA98 or TA100), or a sample to be examined, S9mix and the strain were mixed together, the mixture was multilayered using soft agar on a medium of a test plate, and then incubated at 37° C. for 48 hours. Judgment was made by counting the number of reverse mutation colonies on the plate after the incubation, and when the number of reverse mutation colonies was not less than two times the number in negative control and showed concentration-dependent increase, mutagenicity was determined to be positive.

The results are shown in Table 6. The numbers of reverse mutation colonies of the respective strains in the group treated with Compounds 1, 2 and 4 were less than two times the number in the group treated with the negative control, regardless of addition of S9mix and the addition amount of a sample to be examined. From the aforementioned results, it is judged that Compounds 1, 2 and 4 are negative in the Ames test and have no mutagenicity.

TABLE 6

Results of Ames test

| | | Mutagenicity | | | |
|---|---|---|---|---|---|
| | | Without addition of S9mix | | With addition of S9mix | |
| | Compound | TA98 | TA100 | TA98 | TA100 |
| Example I-18 | Compound 1 | Negative | Negative | Negative | Negative |
| Example I-19 | Compound 2 | Negative | Negative | Negative | Negative |
| Example I-20 | Compound 4 | Negative | Negative | Negative | Negative |

Example II-11, II-12, Comparative Example II-1

Measurement of Transferability into Brain and Clearance

Using the Compounds 10 and 11, a time course change of radioactive accumulation in brain of male Wistar rats (7-week old) was measured.

0.05 mL (20-31 MBq/mL in radioactivity concentration) of a solution of Compound 10 (Example II-11), Compound 11 (Example II-12) and [$^{123}$I]-IMPY (Comparative Example II-1) prepared in the above Reference Example 2 respectively in a 10 mg/mL ascorbic acid-containing physiological saline solution were injected under thiopental anesthesia into the tail vein of respective Wistar rats. The rats were sacrificed by bleeding from abdominal artery, and brains were removed and subjected to measurement of mass of brains and further subjected to measurement of radioactivity (hereinafter referred to as A in this Example) with a single channel analyzer (detector type: SP-20 manufactured by OHYO KOKEN KOGYO Co., Ltd.) 2, 5, 30 and 60 minutes after the injection. Also, radioactivity (hereinafter referred to as B in this Example) of the rest of the whole body was measured in the same manner as above. Using these measurement results, radioactive accumulation per unit weight of brain (% ID/g) at the respective time points were calculated in accordance with the following formula (6).

Three animals were used for experiment at the respective time points.

$$\% \, ID/g = \frac{A}{B \times \text{brain weight}} \times 100 \qquad (6)$$

The results are shown in Table 7. As shown in Table 7, Compounds 10 and 11 showed a significant radioactive accumulation like $^{123}$I-IMPY at the time point of two minutes after the injection, and then showed a tendency to rapidly clear away in 60 minutes. These results suggest that Compounds 10 and 11 possess excellent transferability to brain and rapid clearance from brain like $^{123}$I-IMPY.

TABLE 7

Radioactive accumulation in brain of the present compound after intravenous injection (rats)

|  | Compound | Radioactive accumulation per unit weight (% ID/g) | | | |
|---|---|---|---|---|---|
|  |  | After 2 min. | After 5 min. | After 30 min. | After 60 min. |
| Example II-11 | Compound 10 | 0.62 | 0.33 | 0.08 | 0.02 |
| Example II-12 | Compound 11 | 0.65 | 0.43 | 0.09 | 0.03 |
| Comparative Example II-1 | $^{123}$I-IMPY | 1.19 | 0.97 | 0.23 | 0.09 |

Example II-13

Ex Vivo Autoradiogram of Compound 10 Using Rats of Amyloid Injected Model (1) Aβ$_{1-42}$ (manufactured by Peptide Institute, Inc.) was dissolved in phosphate buffer (pH 7.4) and shaken at 37° C. for 72 hours, to obtain 1 mg/mL of a suspension of aggregated Aβ (hereinafter referred to as amyloid suspension in this Example).

(2) 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) Compound 10 was dissolved in a 10 mg/mL ascorbic acid-containing physiological saline solution to obtain a sample solution (31 MBq/mL in radioactivity concentration in the sample solution). This solution was injected under thiopental anesthesia into the rat through the tail vein (dosage: 0.5 mL, dosed radioactivity: 15 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 14b).

FIG. 14 shows images by autoradiogram and Thioflavin T staining of the brain slice of the rat to which amyloid was injected intracerebrally. As shown in FIG. 14, a marked accumulation of radioactivity was observed in the amygdaloid nucleus on the side to which the amyloid suspension was injected. On the other hand, no significant accumulation of radioactivity was observed in the amygdaloid nucleus on the side to which the physiological saline solution was injected, compared with the other sites. On the autoradiogram, little accumulation of radioactivity was observed at sites other than the site to which amyloid was injected. From the result of Thioflavin T staining, it was confirmed that amyloid was present in the site where radioactivity accumulated (FIG. 14b). These results suggest that Compound 10 possesses a property of accumulating on intracerebral amyloid and a capability of imaging intracerebral amyloid.

Example II-14

Ex Vivo Autoradiogram of Compound 11 Using Rats of Amyloid Injected Model

The same operation as in Example II-13 was conducted except using a solution (radioactive concentration of 30 MBq/mL in a sample solution) of Compound 11 in a 10 mg/mL ascorbic acid solution as a sample solution.

FIG. 15 shows images by autoradiogram and Thioflavin T staining of the brain slice of the rat to which amyloid was injected intracerebrally. As shown in FIG. 15, a marked accumulation of radioactivity was observed in the amygdaloid nucleus on the side to which the amyloid suspension was injected. From the result of Thioflavin T staining, it was confirmed that amyloid was present in the site where radioactivity accumulated (FIG. 15b). On the other hand, no significant accumulation of radioactivity was observed in the amygdaloid nucleus on the side to which the physiological saline solution was injected, compared with the other sites.

These results suggest that Compound 11 possesses a property of accumulating on intracerebral amyloid, and a capability of imaging intracerebral amyloid.

Example II-15

Reverse Mutation Test

In order to examine mutagenicity of Compound 8, reverse mutation test using *Salmonella typhimurium* TA98 and TA100 (hereinafter referred to as Ames test) was conducted.

The test was conducted without addition of S9mix and with addition of S9mix. Dimethylsulfoxide was used as a negative control. A positive control was 2-(2-furyl)-3-(5-nitro-2-furyl) acrylamide in case S9mix was not added, and 2-aminoanthracene in case S9mix was added.

The amount of Compound 8 to be added to the test plate was 7 dosages (geometric ratio 3) with the maximum dose being 5000 µg/plate. After Compound 8 and a strain (TA98 or TA100), or Compound 8, S9mix and the strain were mixed together, the mixture was multilayered using soft agar on a medium of a test plate, and then incubated at 37° C. for 48 hours. Judgment was made by counting the number of reverse mutation colonies on the plate after the incubation, and when the number of reverse mutation colonies was not less than two times the number in negative control and showed concentration-dependent increase, mutagenicity was determined to be positive.

The results are shown in Table 8. The numbers of reverse mutation colonies of the respective strains in the group treated with Compound 8 were less than two times the number in the group treated with the negative control, regardless of addition of S9mix and the addition amount of a sample to be examined. On the other hand, a marked increase in the number of reverse mutation colonies was observed in the group treated with the positive control. From the aforementioned results, it is judged that Compound 8 is negative in the Ames test and has no mutagenicity.

TABLE 8

Results of Ames test

| | | Mutagenicity | | |
| | | Without addition of S9mix | | With addition of S9mix | |
| Compound | | TA98 | TA100 | TA98 | TA100 |
| Example II-15 | Compound 8 | Negative | Negative | Negative | Negative |

INDUSTRIAL APPLICABILITY

The compounds and diagnostic agents of the present invention can be utilized in the field of diagnostics.

Figure 1:
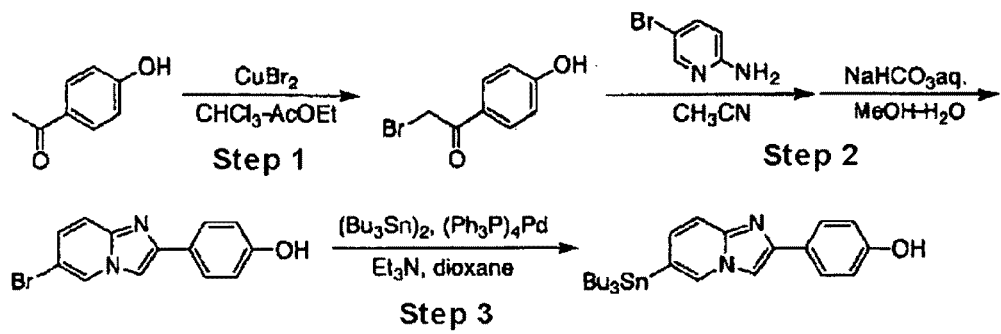
FIG. 1 is a scheme of synthesis of 6-tributylstannyl-2-(4'-hydroxyphenyl)imidazo[1,2-a]pyridine.
Figure 2:
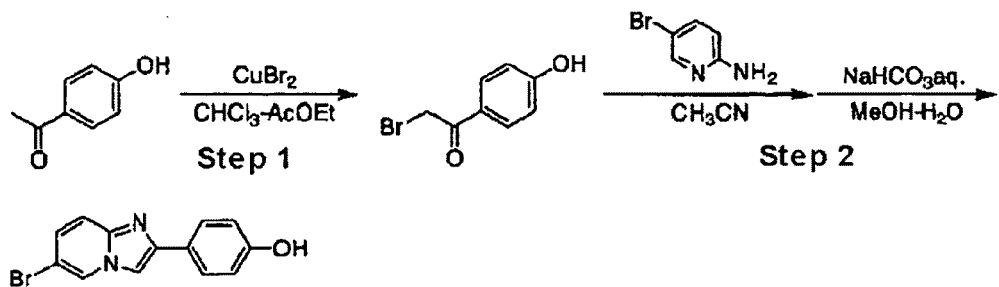
FIG. 2 is a scheme of synthesis of 6-bromo-2-(4'-hydroxyphenyl)imidazo[1,2-a]pyridine.
Figure 3:
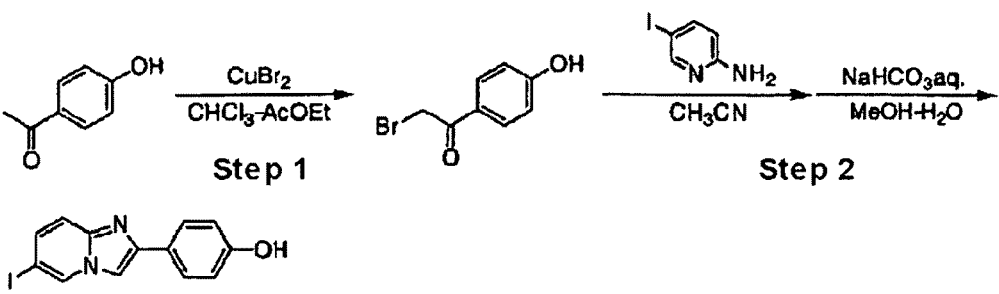
FIG. 3 is a scheme of synthesis of 2-(4'-hydroxyphenyl)-6-iodoimidazo[1,2-a]pyridine.
Figure 4:
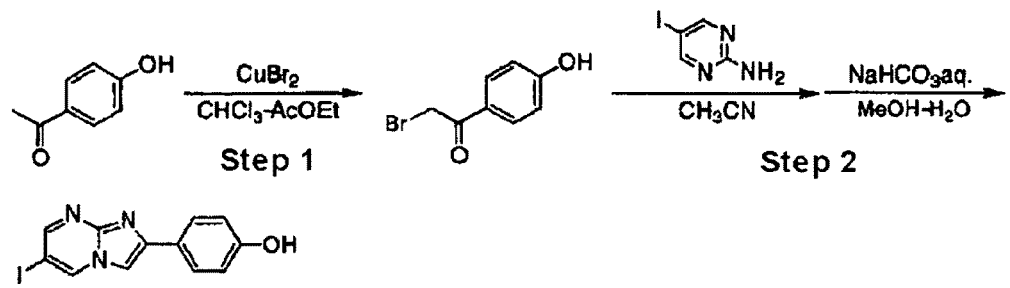
FIG. 4 is a scheme of synthesis of 2-(4'-hydroxyphenyl)-6-iodoimidazo[1,2-a]pyrimidine.
Figure 5:
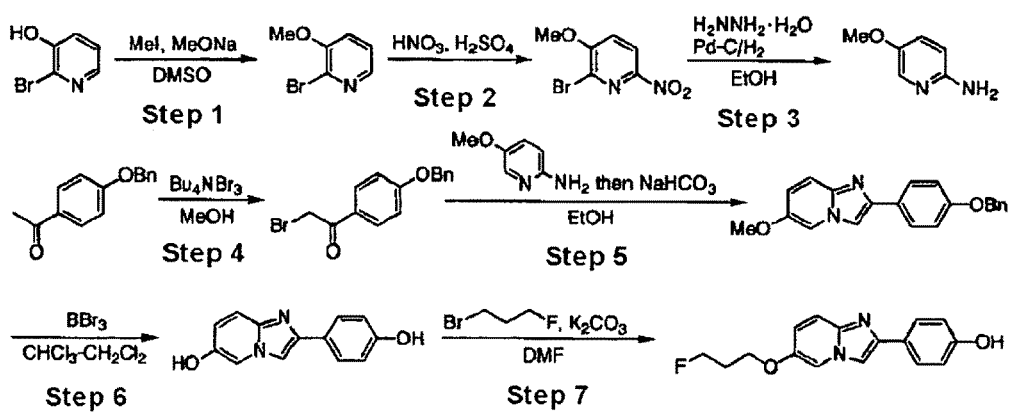
FIG. 5 is a scheme of synthesis of 6-(3'-fluoropropoxy)-2-(4'-hydroxyphenyl)imidazo[1,2-a]pyridine.
Figure 6:
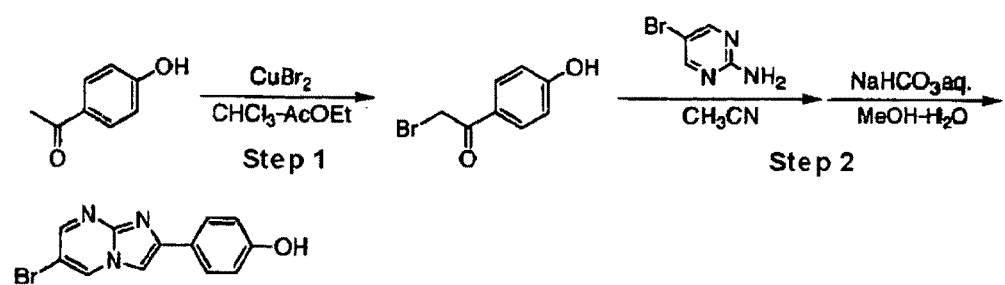
FIG. 6 is a scheme of synthesis of 6-bromo-2-(4'-hydroxyphenyl)imidazo[1,2-a]pyrimidine.
Figure 7:
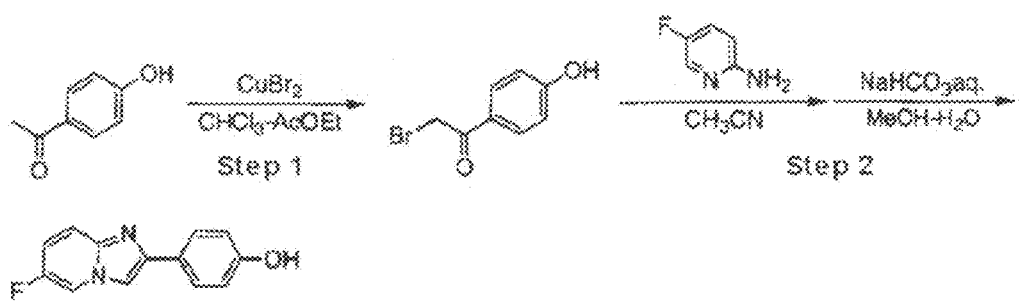
FIG. 7 is a scheme of synthesis of 6-fluoro-2-(4'-hydroxyphenyl)imidazo[1,2-a]pyridine.
Figure 8:
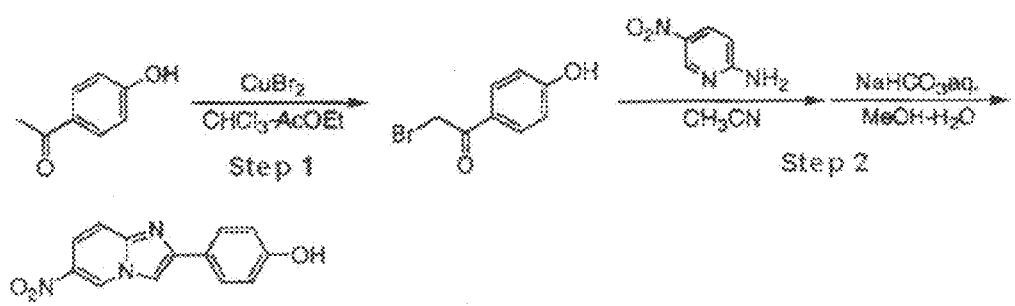
FIG. 8 is a scheme of synthesis of 2-(4'-hydroxyphenyl)-6-nitroimidazo[1,2-a]pyridine.
Figure 9:
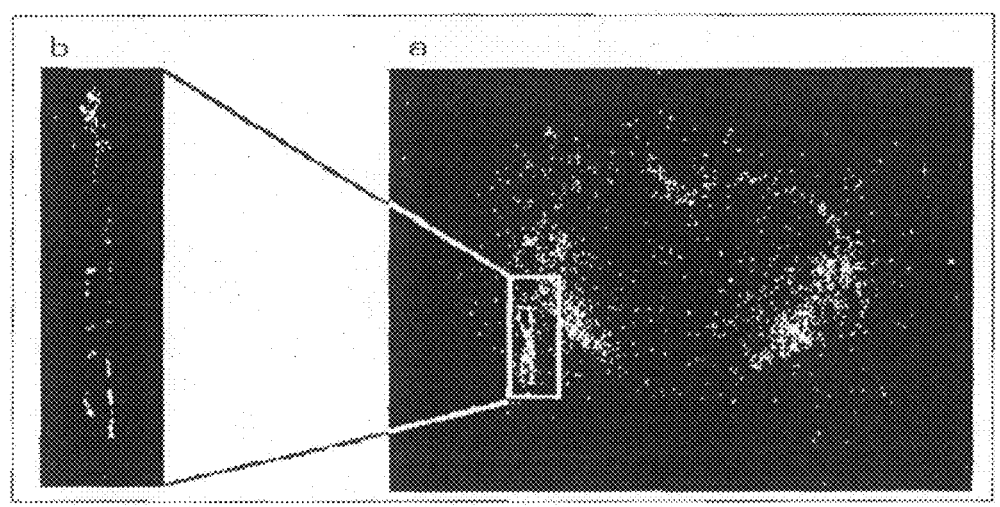
FIG. 9(*a*) is an autoradiogram of the brain slice after the injection of Compound 6, and FIG. 9(*b*) is a fluorescent microscopic image of the Thioflavin T stained sample (a magnification of the site to which the amyloid suspension was injected).
Figure 10:
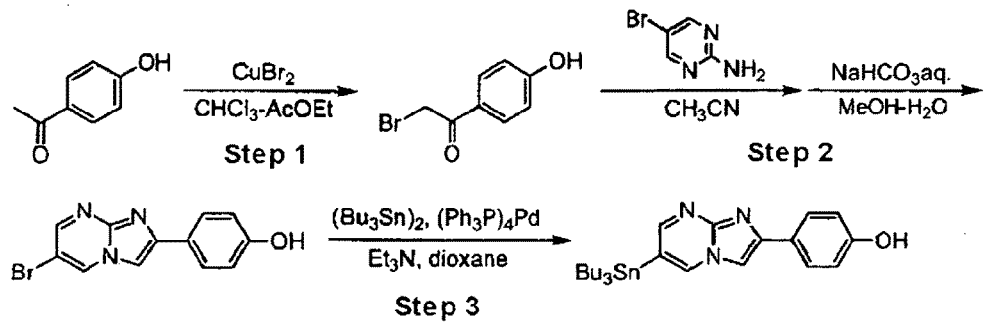
FIG. 10 is a scheme of synthesis of 6-tributylstannyl-2-(4'-hydroxyphenyl)imidazo[1,2-a]pyrimidine.
Figure 11:
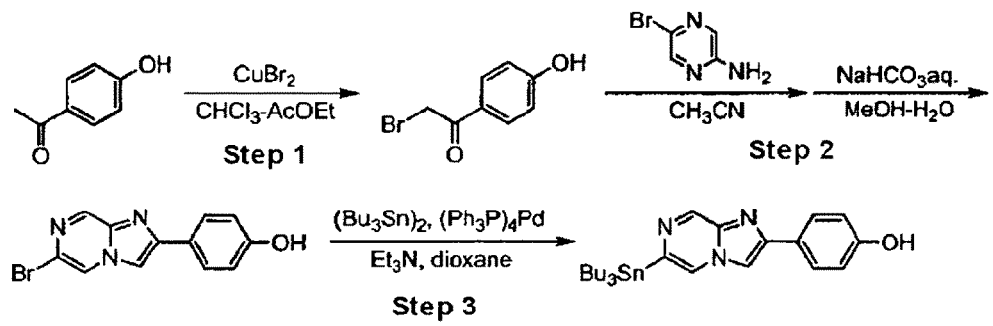
FIG. 11 is a scheme of synthesis of 6-tributylstannyl-2-(4'-hydroxyphenyl)imidazo[1,2-a]pyrazine.
Figure 12:
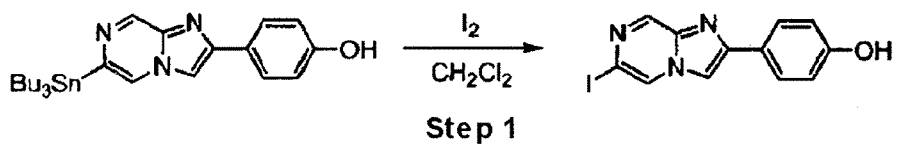
FIG. 12 is a scheme of synthesis of 2-(4'-hydroxyphenyl)-6-iodoimidazo[1,2-a]pyrazine.
Figure 13:
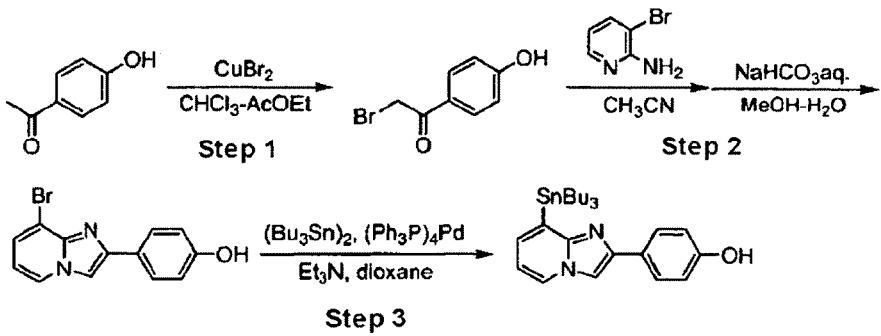
FIG. 13 is a scheme of synthesis of 8-tributylstannyl-2-(4'-hydroxyphenyl)imidazo[1,2-a]pyridine.
Figure 14:
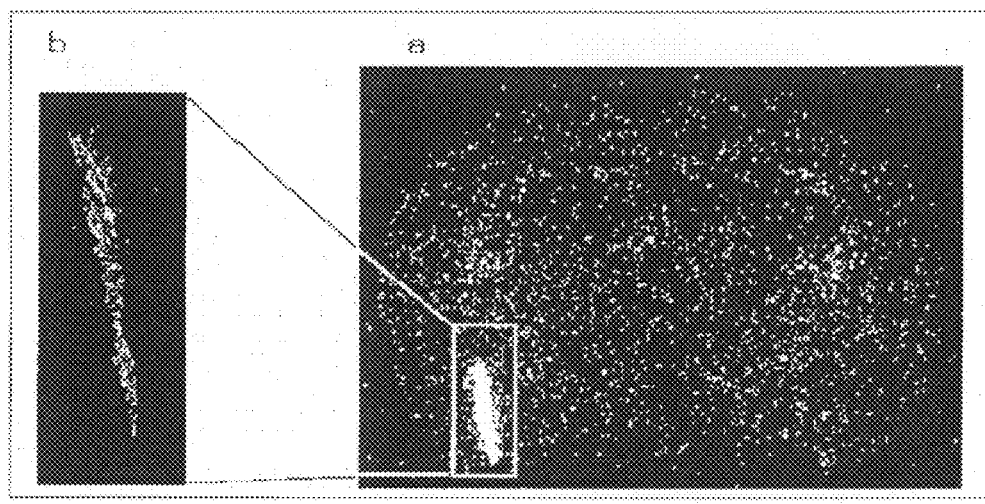
FIG. 14(*a*) is an autoradiogram of the brain slice after the injection of Compound 10, and FIG. 14(*b*) is a fluorescent microscopic image of the Thioflavin T stained sample (a magnification of the site to which the amyloid suspension was injected).
Figure 15:
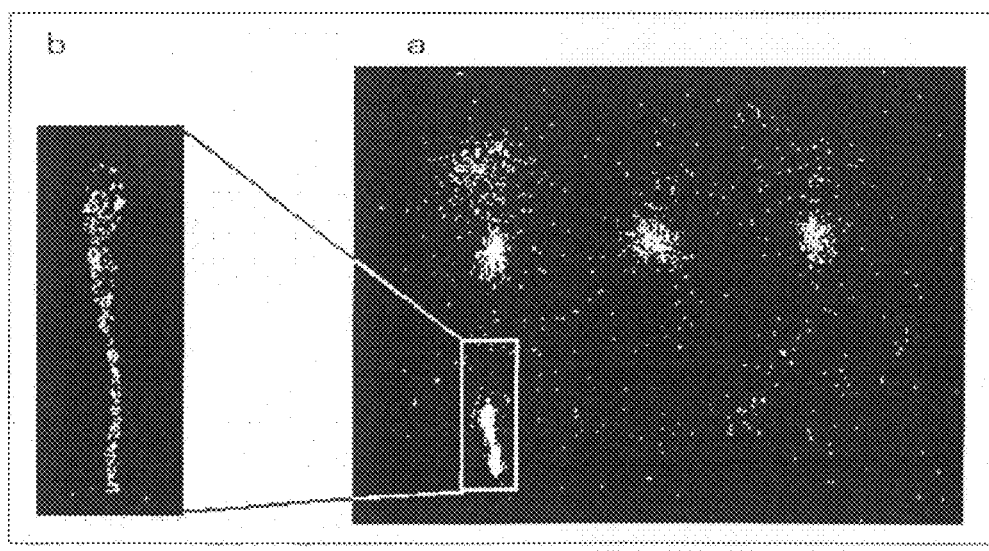
FIG. 15(*a*) is an autoradiogram of the brain slice after the injection of Compound 11, and FIG. 15(*b*) is a fluorescent microscopic image of the Thioflavin T stained sample (a magnification of the site to which the amyloid suspension was injected).

The invention claimed is:

1. A compound represented by the following formula (1), or a pharmaceutically acceptable salt thereof:

(1)

wherein $A^1$, $A^2$, $A^3$ and $A^4$ independently represent a carbon or a nitrogen, and $R^3$ is a group represented by the following formula:

$$R^1 \!-\!\left[\!\begin{array}{c}H_2\\C\end{array}\!\right]_m\!-\!\left[O\right]_n\!-$$

wherein $R^1$ is a radioactive halogen substituent;

m is an integer of 0 to 4; and n is an integer of 0 or 1, provided that at least one of $A^1$, $A^2$, $A^3$ and $A^4$ represents a carbon, and $R^3$ binds to a carbon represented by $A^1$, $A^2$, $A^3$ or $A^4$.

2. A compound or a salt thereof according to claim 1, wherein at least three of $A^1$, $A^2$, $A^3$ and $A^4$ represent carbons.

3. A compound or a salt thereof according to claim 2, wherein all of $A^1$, $A^2$, $A^3$ and $A^4$ represent carbons.

4. A compound or a salt thereof according to claim 1, wherein $R^1$ is selected from the group consisting of $^{18}$F, $^{76}$Br, $^{123}$I, $^{124}$I, $^{125}$I and $^{131}$I.

5. A compound represented by the following formula (2), wherein $A^5$, $A^6$, $A^7$ and $A^8$ independently represent a carbon or a nitrogen, and

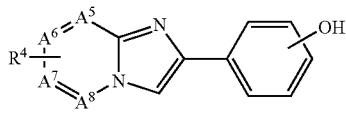 (2)

R⁴ a group represented by the following formula:

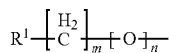

wherein m is an integer of 0 to 4;
n is an integer of 0 or 1; and
when m=n=0, $R^2$ is a non-radioactive halogen substituent, nitro subsituent, trialkylstannyl substituent having 3 to 12 carbon atoms or triphenylstannyl substituent, and when m≠0 and/or n≠0, $R^2$ is a non-radioactive halogen substituent, methanesulfonyloxy substituent, trifluoromethanesulfonyloxy substituent or aromatic sulfonyloxy substituent,
provided that at least one of $A^5$, $A^6$, $A^7$ and $A^8$ represents a carbon, and $R^4$ binds to a carbon represented by $A^5$, $A^6$, $A^7$ or $A^8$.

6. A compound or a salt thereof according to claim 5, wherein at least three of $A^5$, $A^6$, $A^7$ and $A^8$ are carbons.

7. A compound or a salt thereof according to claim 6, wherein all of $A^5$, $A^6$, $A^7$ and $A^8$ represent carbons.

8. A compound or a salt thereof according to claim 5, wherein $R^2$ is selected from the group consisting of iodine, bromine, trimethylstannyl substituent, tributylstannyl substituent, trifluoromethanesulfonyloxy substituent and triphenylstannyl substituent.

* * * * *